US009222103B2

(12) United States Patent
Zipfel et al.

(10) Patent No.: US 9,222,103 B2
(45) Date of Patent: Dec. 29, 2015

(54) METHODS OF ENHANCING THE RESISTANCE OF PLANTS TO BACTERIAL PATHOGENS

(75) Inventors: Cyril B. Zipfel, Norwich (GB); Jonathan D. G. Jones, Norwich (GB)

(73) Assignee: Two Blades Foundation, Evanston, IL (US)

(*) Notice: Subject to any disclaimer, the term of this patent is extended or adjusted under 35 U.S.C. 154(b) by 550 days.

(21) Appl. No.: 12/611,325

(22) Filed: Nov. 3, 2009

(65) Prior Publication Data
US 2010/0122376 A1 May 13, 2010

Related U.S. Application Data

(60) Provisional application No. 61/110,618, filed on Nov. 3, 2008, provisional application No. 61/187,505, filed on Jun. 16, 2009.

(51) Int. Cl.
C12N 15/82 (2006.01)
(52) U.S. Cl.
CPC .................................. C12N 15/8281 (2013.01)
(58) Field of Classification Search
USPC ........................................................ 800/279
See application file for complete search history.

(56) References Cited

U.S. PATENT DOCUMENTS 6,262,343 B1 7/2001 Staskawicz et al.
2007/0214517 A1 9/2007 Alexandrov et al.

OTHER PUBLICATIONS

Zipfel et al. Perception of the bacterial PAMP EF-Tu by the receptor EFR restricts Agrobacterium-mediated transformation (2006) Cell 125: 749-760.*
Tai et al. Expression of the Bs2 pepper gene confers resistance to bacterial spot disease (1999) PNAS 96: 14153-14158.*
Guo et al. Protein tolerance to random amino acid change (2004) PNAS 101: 9205-9210.*
Zipfel et al. (206) Cell 125: 749-760.*
Tai et al. (1999) PNAS 96: 14153-14158.*
Zipfel et al., "Perception of the Bacterial PAMP EF-Tu by the Receptor EFR Restricts Agrobacterium-Mediated Transformation," Cell, 2006, vol. 125, pp. 749-760.
Bent, A., et al., "Elicitors, Effectors, and RGenes: The New Paradigm and a Lifetime Supply of Questions," Annu. Rev. Phytopathol., 2007, vol. 45, pp. 399-436.
Ellis, J., "Structure, function and evolution of plant disease resistance genes," Curr. Opin. Plant Biol., 2000, vol. 3, pp. 278-284.
Jones, J., et al., "The plant immune system," Nature, 2006, vol. 444, pp. 323-329.
Kunze, G., et al., "The N Terminus of Bacterial Elongation Factor Tu Elicits Innate Immunity in Arabidopsis Plants," The Plant Cell, 2004, vol. 16, pp. 3496-3507.

NCBI Database Accession No. NM_127974, "Arabidopsis thaliana putative leucine-rich repeat transmembrane protein kinase (AT2G24130) mRNA, complete cds," 2011, pp. 1-3.
NCBI Database Accession No. NM_114576, "Arabidopsis thaliana leucine-rich repeat protein kinase-like protein (AT3G47090) mRNA, complete cds," 2011, pp. 1-3.
NCBI Database Accession No. NM_114578, "Arabidopsis thaliana leucine-rich repeat protein kinase-like protein (AT3G47110) mRNA, complete cds," 2011, pp. 1-3.
NCBI Database Accession No. NM_114625, "Arabidopsis thaliana putative LRR receptor-like serine/threonine-protein kinase (AT3G47570) mRNA, complete cds," 2011, pp. 1-3.
NCBI Database Accession No. NM_114626, "Arabidopsis thaliana leucine-rich repeat protein kinase-like protein (AT3G47580) mRNA, complete cds," 2011, pp. 1-3.
NCBI Database Accession No. NM_123301, "Arabidopsis thaliana leucine-rich repeat protein kinase-like protein (AT5G39390) mRNA, complete cds," 2011, pp. 1-2.
NCBI Database Accession No. NM_122055, "Arabidopsis thaliana LRR receptor-like serine/threonine-protein kinase EFR (EFR) mRNA, complete cds," 2011, pp. 1-3.
Römer, P., et al., "Plant Pathogen Recognition Mediated by Promoter Activation of the Pepper Bs3 Resistance Gene," Science, 2007, vol. 318, pp. 645-648.
Tameling, W., et al., "Resistance proteins: scouts of the plant innate immune system," Eur J Plant Pathol, 2008, vol. 121, pp. 243-255.
Zipfel, C., et al., "Bacterial disease resistance in Arabidopsis through flagellin perception," Nature, 2004, vol. 428, pp. 764-767.
Zipfel, C., et al., "Plants and animals: a different taste for microbes?," Current Opinion in Plant Biology, 2005, vol. 8, pp. 353-360.
Alfano, J. and A. Collmer, "Type III Secretion System Effector Proteins: Double Agents in Bacterial Disease and Plant Defense," Annu. Rev. Phytopathol., 2004, pp. 385-414, vol. 42.
Brutus, A. and S.Y. He, "Broad-spectrum defense against plant pathogens," Nature Biotechnology, Apr. 2010, pp. 330-331, vol. 28(4).
Chisholm, S., et al., "Host-Microbe Interactions: Shaping the Evolution of the Plant Immune Response,"Cell, Feb. 24, 2006, pp. 803-814, vol. 124, Elsevier Inc.
Eitas, T.K. and J.L. Dangl, "NB-LRR proteins: Pairs, pieces, perception, partners and pathways," Curr. Opin. Plant Biol., Aug. 1, 2010, pp. 472-477, vol. 13(4), Elsevier Ltd.
He, et al., "Specific Bacterial Suppressors and MAMP Signaling Upstream of MAPKKK in Arabidopsis Innate Immunity," Cell, May 5, 2006, pp. 563-575, vol. 125, Elsevier Inc.

(Continued)

Primary Examiner — Steven Bernacki
(74) Attorney, Agent, or Firm — Williams Mullen, PC; David M. Saravitz

(57) ABSTRACT

Methods are provided for enhancing the resistance of plants to bacterial pathogens. The methods involve transforming a plant with a polynucleotide molecule comprising a plant promoter operably linked to a nucleotide sequence that encodes a plant receptor that binds specifically with bacterial elongation factor-Tu. Further provided are expression cassettes, transformed plants, seeds, and plant cells that are produced by such methods.

10 Claims, 14 Drawing Sheets

(56) References Cited

OTHER PUBLICATIONS

Lacombe, et al., "Interfamily transfer of a plant pattern-recognition receptor confers broad-spectrum bacterial resistance," *Nature Biotechnology*, Apr. 2010, pp. 1-6, vol. 28(4), Nature America, Inc.

Shan, et al., "Bacterial Effectors Target the Common Signaling Partner BAK1 to Disrupt Multiple MAMP Receptor-Signaling Complexes and Impede Plant Immunity," *Cell Host Microbe*, Jul. 17, 2008, pp. 1-21, vol. 4(1), Elsevier Inc.

* cited by examiner

*Xcc 8004, Xcc B100*
MARAKFLREKLHVNVGTI (SEQ ID NO: 6)

*X.c musacearum, X. axonopodis pv citri, X. campestris pv vesicatoria 85-10, Xanthomonas oryzae pv oryzae MAFF311018*
MAKAKFERTKPHVNVGTI (SEQ ID NO: 7)

*Ralstonia solanacearum*
MAKEKFERTKPHVNVGTI (SEQ ID NO: 8)

*Pto DC3000*
MAKEKFDRSLPHCNVGTI (SEQ ID NO: 9)

*Psp 1448a, Pss B728a, Pf0-1*
MAKEKFDRSLPHVNVGTI (SEQ ID NO: 10)

*Pf-5*
MAKEKFERNKPHVNVGTI (SEQ ID NO: 11)

*Dickeya, Pectobacterium atrosepticum*
MSKEKFERTKPHVNVGTI (SEQ ID NO: 12)

*Candidatus Liberibacter asiaticus str. Psy62*
MVEKRYVRNKESLGLSTI (SEQ ID NO: 13)

FIG. 7

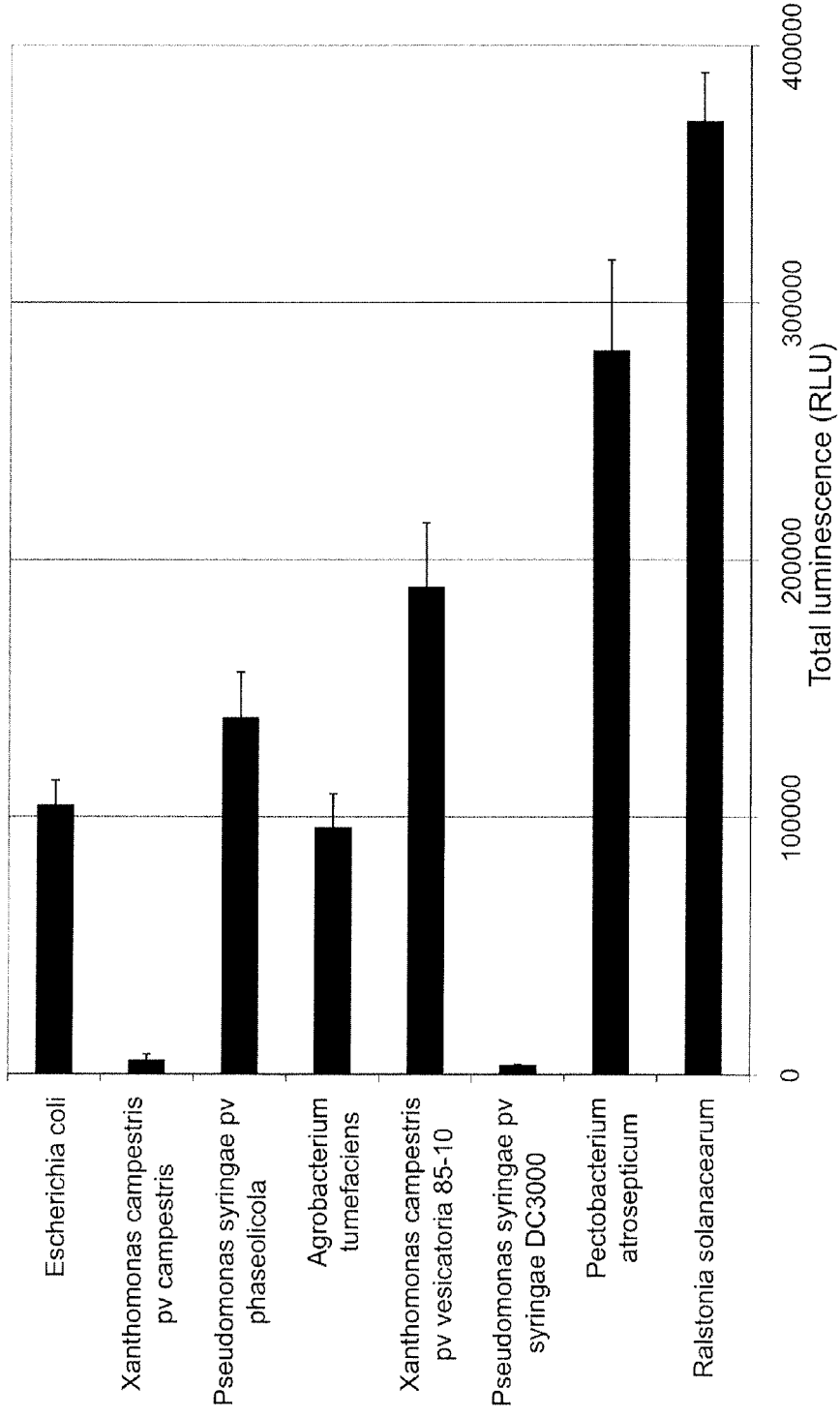

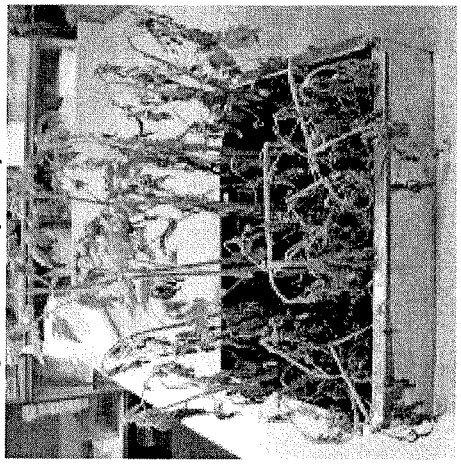
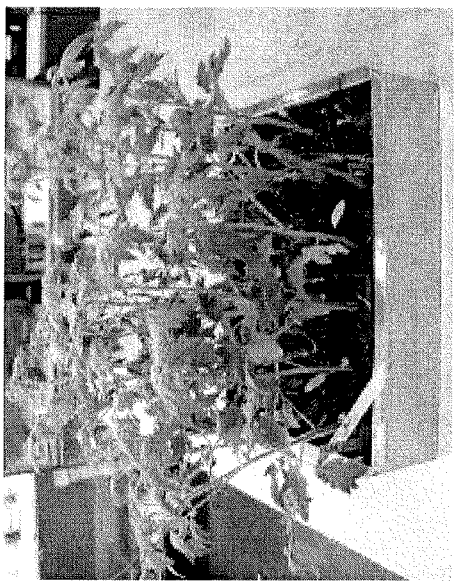
FIG. 9

SEQUENCE LISTING

<160> NUMBER OF SEQ ID NOS: 13

<210> SEQ ID NO 1
<211> LENGTH: 3096
<212> TYPE: DNA
<213> ORGANISM: Arabidopsis thaliana
<220> FEATURE:
<221> NAME/KEY: CDS
<222> LOCATION: (1)...(3096)

<400> SEQUENCE: 1

```
atg aag ctg tcc ttt tca ctt gtt ttc aat gct ctc acg ttg ctt ctt        48
Met Lys Leu Ser Phe Ser Leu Val Phe Asn Ala Leu Thr Leu Leu Leu
1               5                   10                  15 caa gtt tgc atc ttt gct caa gcc agg ttt tct aat gag act gat atg        96
Gln Val Cys Ile Phe Ala Gln Ala Arg Phe Ser Asn Glu Thr Asp Met
            20                  25                  30 caa gct ttg ctt gag ttc aag tct caa gtt tct gaa aac aac aag aga       144
Gln Ala Leu Leu Glu Phe Lys Ser Gln Val Ser Glu Asn Asn Lys Arg
        35                  40                  45 gag gtc ttg gct tca tgg aat cac tcc tcc cca ttt tgt aat tgg att       192
Glu Val Leu Ala Ser Trp Asn His Ser Ser Pro Phe Cys Asn Trp Ile
    50                  55                  60 gga gtc aca tgt ggc cgc agg aga gaa aga gtt ata agt ttg aac ctt       240
Gly Val Thr Cys Gly Arg Arg Arg Glu Arg Val Ile Ser Leu Asn Leu
65                  70                  75                  80 gga gga ttc aag tta acc ggt gtg atc tca ccc tcc att ggt aat ctc       288
Gly Gly Phe Lys Leu Thr Gly Val Ile Ser Pro Ser Ile Gly Asn Leu
                85                  90                  95 tcc ttt ctt aga tta ctt aat ctt gca gac aac tct ttt gga agt acc       336
Ser Phe Leu Arg Leu Leu Asn Leu Ala Asp Asn Ser Phe Gly Ser Thr
            100                 105                 110 atc cct caa aag gtg gga agg cta ttt agg ctt cag tac ttg aac atg       384
Ile Pro Gln Lys Val Gly Arg Leu Phe Arg Leu Gln Tyr Leu Asn Met
        115                 120                 125 agc tat aat ctc ctc gaa gga agg att ccg tct agt ctt tct aac tgc       432
Ser Tyr Asn Leu Leu Glu Gly Arg Ile Pro Ser Ser Leu Ser Asn Cys
    130                 135                 140
```

-continued

| | |
|---|---|
| tct aga ctg tcg acc gtt gat tta tcg tca aac cat ctt gga cat ggt<br>Ser Arg Leu Ser Thr Val Asp Leu Ser Ser Asn His Leu Gly His Gly<br>145                        150                      155                     160 | 480 |
| gtt cct tca gaa cta ggt tca ctt tct aag ctt gcc att ctg gat ctt<br>Val Pro Ser Glu Leu Gly Ser Leu Ser Lys Leu Ala Ile Leu Asp Leu<br>                      165                     170                     175 | 528 |
| agc aaa aac aac ctt act gga aat ttt cct gca tct tta gga aac ttg<br>Ser Lys Asn Asn Leu Thr Gly Asn Phe Pro Ala Ser Leu Gly Asn Leu<br>           180                     185                     190 | 576 |
| acg tca ctt cag aag ctt gac ttt gca tat aac cag atg aga ggt gag<br>Thr Ser Leu Gln Lys Leu Asp Phe Ala Tyr Asn Gln Met Arg Gly Glu<br>195                        200                     205 | 624 |
| att cca gac gaa gta gct aga ttg act caa atg gtg ttt ttc caa ata<br>Ile Pro Asp Glu Val Ala Arg Leu Thr Gln Met Val Phe Phe Gln Ile<br>       210                     215                     220 | 672 |
| gca ctg aat agt ttt tca ggt ggt ttt cct cct gca ttg tac aac atc<br>Ala Leu Asn Ser Phe Ser Gly Gly Phe Pro Pro Ala Leu Tyr Asn Ile<br>225                        230                     235                     240 | 720 |
| tcc tct ctt gag tct cta tct cta gct gac aat agc ttt tcg ggt aat<br>Ser Ser Leu Glu Ser Leu Ser Leu Ala Asp Asn Ser Phe Ser Gly Asn<br>                      245                     250                     255 | 768 |
| ctt agg gct gat ttt ggt tat ctt cta cca aat cta aga aga ctt ctt<br>Leu Arg Ala Asp Phe Gly Tyr Leu Leu Pro Asn Leu Arg Arg Leu Leu<br>           260                     265                     270 | 816 |
| ttg gga aca aat cag ttc act gga gct att ccc aaa aca ctt gcc aat<br>Leu Gly Thr Asn Gln Phe Thr Gly Ala Ile Pro Lys Thr Leu Ala Asn<br>275                        280                     285 | 864 |
| atc tca agc ctt gaa agg ttt gat atc tca tct aat tac ctg tct ggt<br>Ile Ser Ser Leu Glu Arg Phe Asp Ile Ser Ser Asn Tyr Leu Ser Gly<br>       290                     295                     300 | 912 |
| agt atc cct ttg agc ttt gga aag tta cgt aat ctg tgg tgg tta ggg<br>Ser Ile Pro Leu Ser Phe Gly Lys Leu Arg Asn Leu Trp Trp Leu Gly<br>305                        310                     315                     320 | 960 |
| att cgt aat aac tct ctt gga aat aac tcg tcc agt ggt ctt gaa ttt<br>Ile Arg Asn Asn Ser Leu Gly Asn Asn Ser Ser Ser Gly Leu Glu Phe<br>                      325                     330                     335 | 1008 |
| att ggg gct gtg gcg aac tgc act caa tta gag tac tta gat gtt ggt<br>Ile Gly Ala Val Ala Asn Cys Thr Gln Leu Glu Tyr Leu Asp Val Gly<br>           340                     345                     350 | 1056 |
| tac aat aga ctt gga ggt gag ctt cct gct tct ata gcc aat ctg tcc<br>Tyr Asn Arg Leu Gly Gly Glu Leu Pro Ala Ser Ile Ala Asn Leu Ser<br>355                        360                     365 | 1104 |
| act aca ttg act agt ctg ttc ctt gga caa aat ctt atc tct gga acc<br>Thr Thr Leu Thr Ser Leu Phe Leu Gly Gln Asn Leu Ile Ser Gly Thr<br>       370                     375                     380 | 1152 |
| att cct cat gac atc ggg aat ctt gta agc ctg caa gaa ctc agc tta<br>Ile Pro His Asp Ile Gly Asn Leu Val Ser Leu Gln Glu Leu Ser Leu<br>385                        390                     395                     400 | 1200 |
| gaa aca aat atg ttg agt gga gaa ctt ccc gtc tct ttc ggg aag ctt<br>Glu Thr Asn Met Leu Ser Gly Glu Leu Pro Val Ser Phe Gly Lys Leu<br>                      405                     410                     415 | 1248 |
| ttg aac ttg cag gtt gtg gat ctg tat tca aat gca ata tcg ggg gaa<br>Leu Asn Leu Gln Val Val Asp Leu Tyr Ser Asn Ala Ile Ser Gly Glu<br>           420                     425                     430 | 1296 |
| ata cca tct tat ttt ggc aac atg act cgg ttg cag aag ctc cat ttg<br>Ile Pro Ser Tyr Phe Gly Asn Met Thr Arg Leu Gln Lys Leu His Leu<br>435                        440                     445 | 1344 |
| aat agc aat agt ttc cac gga aga atc cct cag agt ctt gga cgt tgt<br>Asn Ser Asn Ser Phe His Gly Arg Ile Pro Gln Ser Leu Gly Arg Cys<br>       450                     455                     460 | 1392 |

```
cga tac ttg cta gac ctg tgg atg gat aca aat agg ttg aat ggg act    1440
Arg Tyr Leu Leu Asp Leu Trp Met Asp Thr Asn Arg Leu Asn Gly Thr
465                 470                 475                 480 ata cct cag gaa ata ctg caa att cca tcc ctc gct tac ata gat ttg    1488
Ile Pro Gln Glu Ile Leu Gln Ile Pro Ser Leu Ala Tyr Ile Asp Leu
                485                 490                 495 tca aac aat ttc ttg aca ggc cat ttt cca gaa gaa gtt gga aag tta    1536
Ser Asn Asn Phe Leu Thr Gly His Phe Pro Glu Glu Val Gly Lys Leu
            500                 505                 510 gaa ctt ctt gtt gga cta ggt gct tcg tac aac aaa tta tca gga aag    1584
Glu Leu Leu Val Gly Leu Gly Ala Ser Tyr Asn Lys Leu Ser Gly Lys
        515                 520                 525 atg cca caa gct ata ggg ggt tgt ctt tcg atg gaa ttt ctc ttt atg    1632
Met Pro Gln Ala Ile Gly Gly Cys Leu Ser Met Glu Phe Leu Phe Met
530                 535                 540 caa gga aat tcg ttt gac gga gcc att cca gat ata agc cgg ttg gta    1680
Gln Gly Asn Ser Phe Asp Gly Ala Ile Pro Asp Ile Ser Arg Leu Val
545                 550                 555                 560 agc cta aag aat gtt gac ttc tcc aac aac aat ctc tct ggc cgg ata    1728
Ser Leu Lys Asn Val Asp Phe Ser Asn Asn Asn Leu Ser Gly Arg Ile
                565                 570                 575 cct cga tat ctg gcc agt ctt cct tcg ctg cga aat ctg aat ctt tct    1776
Pro Arg Tyr Leu Ala Ser Leu Pro Ser Leu Arg Asn Leu Asn Leu Ser
            580                 585                 590 atg aac aag ttt gag gga agg gtg cca aca aca gga gtg ttt cga aat    1824
Met Asn Lys Phe Glu Gly Arg Val Pro Thr Thr Gly Val Phe Arg Asn
        595                 600                 605 gct aca gca gtt tct gtt ttt ggt aac aca aat att tgc gga ggc gtc    1872
Ala Thr Ala Val Ser Val Phe Gly Asn Thr Asn Ile Cys Gly Gly Val
610                 615                 620 cga gaa atg caa cta aag cca tgc att gta cag gca tct cca agg aag    1920
Arg Glu Met Gln Leu Lys Pro Cys Ile Val Gln Ala Ser Pro Arg Lys
625                 630                 635                 640 aga aag cct ctg tca gtt aga aag aaa gtt gtc agt ggt att tgt ata    1968
Arg Lys Pro Leu Ser Val Arg Lys Lys Val Val Ser Gly Ile Cys Ile
                645                 650                 655 ggt ata gct tcg ctt ttg tta atc ata att gtg gct tct ctg tgt tgg    2016
Gly Ile Ala Ser Leu Leu Leu Ile Ile Ile Val Ala Ser Leu Cys Trp
            660                 665                 670 ttc atg aag agg aaa aag aaa aac aat gcc agt gat ggt aac cca tct    2064
Phe Met Lys Arg Lys Lys Lys Asn Asn Ala Ser Asp Gly Asn Pro Ser
        675                 680                 685 gat tct act act ttg ggg atg ttc cat gag aag gta agt tat gaa gag    2112
Asp Ser Thr Thr Leu Gly Met Phe His Glu Lys Val Ser Tyr Glu Glu
690                 695                 700 ctt cat agt gca aca agt cgc ttc tct tca acc aat ttg att ggt tca    2160
Leu His Ser Ala Thr Ser Arg Phe Ser Ser Thr Asn Leu Ile Gly Ser
705                 710                 715                 720 ggc aat ttc ggt aat gtg ttt aaa gga ttg ctt ggc cct gag aat aaa    2208
Gly Asn Phe Gly Asn Val Phe Lys Gly Leu Leu Gly Pro Glu Asn Lys
                725                 730                 735 ctc gtc gcg gtt aaa gtt ttg aac ctc cta aag cat gga gcg acg aaa    2256
Leu Val Ala Val Lys Val Leu Asn Leu Leu Lys His Gly Ala Thr Lys
            740                 745                 750 agc ttt atg gcg gaa tgt gaa acc ttc aag ggt ata cga cat cgt aac    2304
Ser Phe Met Ala Glu Cys Glu Thr Phe Lys Gly Ile Arg His Arg Asn
        755                 760                 765 ctt gta aaa ctg ata acg gtt tgt tca agc ctt gat tcc gag gga aat    2352
Leu Val Lys Leu Ile Thr Val Cys Ser Ser Leu Asp Ser Glu Gly Asn
```

```
                    770                 775                 780
gat ttc aga gct ctg gtc tat gag ttc atg cca aaa gga agt ctg gat    2400
Asp Phe Arg Ala Leu Val Tyr Glu Phe Met Pro Lys Gly Ser Leu Asp
785                 790                 795                 800 atg tgg ctg cag cta gaa gat ctg gaa agg gta aac gat cac tcg aga    2448
Met Trp Leu Gln Leu Glu Asp Leu Glu Arg Val Asn Asp His Ser Arg
                805                 810                 815 tct tta aca ccc gca gag aaa ctc aac ata gca ata gat gtg gct tca    2496
Ser Leu Thr Pro Ala Glu Lys Leu Asn Ile Ala Ile Asp Val Ala Ser
            820                 825                 830 gct ttg gag tat ctg cac gtt cat tgt cat gac cct gta gct cac tgt    2544
Ala Leu Glu Tyr Leu His Val His Cys His Asp Pro Val Ala His Cys
        835                 840                 845 gat att aag cca agc aac att ctt cta gac gat gat ctg act gct cat    2592
Asp Ile Lys Pro Ser Asn Ile Leu Leu Asp Asp Asp Leu Thr Ala His
    850                 855                 860 gtt agt gac ttt ggt ttg gct cag ctc ctc tat aaa tac gat cga gaa    2640
Val Ser Asp Phe Gly Leu Ala Gln Leu Leu Tyr Lys Tyr Asp Arg Glu
865                 870                 875                 880 tcc ttt cta aac cag ttt agt tct gct ggt gtc aga ggc acc att ggc    2688
Ser Phe Leu Asn Gln Phe Ser Ser Ala Gly Val Arg Gly Thr Ile Gly
                885                 890                 895 tat gcc gcg cca gag tat gga atg gga ggc caa cca tca ata caa gga    2736
Tyr Ala Ala Pro Glu Tyr Gly Met Gly Gly Gln Pro Ser Ile Gln Gly
            900                 905                 910 gat gtg tac agc ttc gga att cta ctt ttg gag atg ttt agt gga aag    2784
Asp Val Tyr Ser Phe Gly Ile Leu Leu Leu Glu Met Phe Ser Gly Lys
        915                 920                 925 aaa cca aca gat gaa tca ttt gca ggc gat tat aac ctc cac agc tac    2832
Lys Pro Thr Asp Glu Ser Phe Ala Gly Asp Tyr Asn Leu His Ser Tyr
    930                 935                 940 aca aag tct ata tta tcg ggt tgc acg agc agt gga ggc agc aac gcc    2880
Thr Lys Ser Ile Leu Ser Gly Cys Thr Ser Ser Gly Gly Ser Asn Ala
945                 950                 955                 960 att gat gag ggg ttg aga ctg gtt ttg cag gtg ggg ata aag tgt tct    2928
Ile Asp Glu Gly Leu Arg Leu Val Leu Gln Val Gly Ile Lys Cys Ser
                965                 970                 975 gaa gaa tat ccg agg gat agg atg aga acg gat gaa gca gta cga gaa    2976
Glu Glu Tyr Pro Arg Asp Arg Met Arg Thr Asp Glu Ala Val Arg Glu
            980                 985                 990 tta atc tca ata aga tct aag ttc ttc agt tcc aag acg act att aca    3024
Leu Ile Ser Ile Arg Ser Lys Phe Phe Ser Ser Lys Thr Thr Ile Thr
        995                 1000                1005 gag agt cct cga gat gct ccg caa agt tct cct cag gaa tgg atg tta    3072
Glu Ser Pro Arg Asp Ala Pro Gln Ser Ser Pro Gln Glu Trp Met Leu
    1010                1015                1020 aat acg gac atg cat act atg tag                                    3096
Asn Thr Asp Met His Thr Met *
1025                1030

<210> SEQ ID NO 2
<211> LENGTH: 1031
<212> TYPE: PRT
<213> ORGANISM: Arabidopsis thaliana

<400> SEQUENCE: 2

Met Lys Leu Ser Phe Ser Leu Val Phe Asn Ala Leu Thr Leu Leu Leu
1               5                   10                  15

Gln Val Cys Ile Phe Ala Gln Ala Arg Phe Ser Asn Glu Thr Asp Met
            20                  25                  30
```

-continued

```
Gln Ala Leu Leu Glu Phe Lys Ser Gln Val Ser Glu Asn Asn Lys Arg
             35                  40                  45

Glu Val Leu Ala Ser Trp Asn His Ser Ser Pro Phe Cys Asn Trp Ile
 50                  55                  60

Gly Val Thr Cys Gly Arg Arg Glu Arg Val Ile Ser Leu Asn Leu
 65                  70                  75                  80

Gly Gly Phe Lys Leu Thr Gly Val Ile Ser Pro Ser Ile Gly Asn Leu
                 85                  90                  95

Ser Phe Leu Arg Leu Leu Asn Leu Ala Asp Asn Ser Phe Gly Ser Thr
                100                 105                 110

Ile Pro Gln Lys Val Gly Arg Leu Phe Arg Leu Gln Tyr Leu Asn Met
            115                 120                 125

Ser Tyr Asn Leu Leu Glu Gly Arg Ile Pro Ser Ser Leu Ser Asn Cys
        130                 135                 140

Ser Arg Leu Ser Thr Val Asp Leu Ser Ser Asn His Leu Gly His Gly
145                 150                 155                 160

Val Pro Ser Glu Leu Gly Ser Leu Ser Lys Leu Ala Ile Leu Asp Leu
                165                 170                 175

Ser Lys Asn Asn Leu Thr Gly Asn Phe Pro Ala Ser Leu Gly Asn Leu
            180                 185                 190

Thr Ser Leu Gln Lys Leu Asp Phe Ala Tyr Asn Gln Met Arg Gly Glu
        195                 200                 205

Ile Pro Asp Glu Val Ala Arg Leu Thr Gln Met Val Phe Phe Gln Ile
210                 215                 220

Ala Leu Asn Ser Phe Ser Gly Gly Phe Pro Pro Ala Leu Tyr Asn Ile
225                 230                 235                 240

Ser Ser Leu Glu Ser Leu Ser Leu Ala Asp Asn Ser Phe Ser Gly Asn
                245                 250                 255

Leu Arg Ala Asp Phe Gly Tyr Leu Leu Pro Asn Leu Arg Arg Leu Leu
            260                 265                 270

Leu Gly Thr Asn Gln Phe Thr Gly Ala Ile Pro Lys Thr Leu Ala Asn
        275                 280                 285

Ile Ser Ser Leu Glu Arg Phe Asp Ile Ser Ser Asn Tyr Leu Ser Gly
        290                 295                 300

Ser Ile Pro Leu Ser Phe Gly Lys Leu Arg Asn Leu Trp Trp Leu Gly
305                 310                 315                 320

Ile Arg Asn Asn Ser Leu Gly Asn Asn Ser Ser Gly Leu Glu Phe
                325                 330                 335

Ile Gly Ala Val Ala Asn Cys Thr Gln Leu Glu Tyr Leu Asp Val Gly
            340                 345                 350

Tyr Asn Arg Leu Gly Gly Glu Leu Pro Ala Ser Ile Ala Asn Leu Ser
        355                 360                 365

Thr Thr Leu Thr Ser Leu Phe Leu Gly Gln Asn Leu Ile Ser Gly Thr
370                 375                 380

Ile Pro His Asp Ile Gly Asn Leu Val Ser Leu Gln Glu Leu Ser Leu
385                 390                 395                 400

Glu Thr Asn Met Leu Ser Gly Glu Leu Pro Val Ser Phe Gly Lys Leu
                405                 410                 415

Leu Asn Leu Gln Val Val Asp Leu Tyr Ser Asn Ala Ile Ser Gly Glu
            420                 425                 430

Ile Pro Ser Tyr Phe Gly Asn Met Thr Arg Leu Gln Lys Leu His Leu
        435                 440                 445
```

```
Asn Ser Asn Ser Phe His Gly Arg Ile Pro Gln Ser Leu Gly Arg Cys
450                 455                 460

Arg Tyr Leu Leu Asp Leu Trp Met Asp Thr Asn Arg Leu Asn Gly Thr
465                 470                 475                 480

Ile Pro Gln Glu Ile Leu Gln Ile Pro Ser Leu Ala Tyr Ile Asp Leu
                485                 490                 495

Ser Asn Asn Phe Leu Thr Gly His Phe Pro Glu Glu Val Gly Lys Leu
            500                 505                 510

Glu Leu Leu Val Gly Leu Gly Ala Ser Tyr Asn Lys Leu Ser Gly Lys
        515                 520                 525

Met Pro Gln Ala Ile Gly Gly Cys Leu Ser Met Glu Phe Leu Phe Met
530                 535                 540

Gln Gly Asn Ser Phe Asp Gly Ala Ile Pro Asp Ile Ser Arg Leu Val
545                 550                 555                 560

Ser Leu Lys Asn Val Asp Phe Ser Asn Asn Asn Leu Ser Gly Arg Ile
                565                 570                 575

Pro Arg Tyr Leu Ala Ser Leu Pro Ser Leu Arg Asn Leu Asn Leu Ser
            580                 585                 590

Met Asn Lys Phe Glu Gly Arg Val Pro Thr Thr Gly Val Phe Arg Asn
        595                 600                 605

Ala Thr Ala Val Ser Val Phe Gly Asn Thr Asn Ile Cys Gly Gly Val
610                 615                 620

Arg Glu Met Gln Leu Lys Pro Cys Ile Val Gln Ala Ser Pro Arg Lys
625                 630                 635                 640

Arg Lys Pro Leu Ser Val Arg Lys Lys Val Ser Gly Ile Cys Ile
                645                 650                 655

Gly Ile Ala Ser Leu Leu Leu Ile Ile Ile Val Ala Ser Leu Cys Trp
            660                 665                 670

Phe Met Lys Arg Lys Lys Asn Asn Ala Ser Asp Gly Asn Pro Ser
        675                 680                 685

Asp Ser Thr Thr Leu Gly Met Phe His Glu Lys Val Ser Tyr Glu Glu
690                 695                 700

Leu His Ser Ala Thr Ser Arg Phe Ser Ser Thr Asn Leu Ile Gly Ser
705                 710                 715                 720

Gly Asn Phe Gly Asn Val Phe Lys Gly Leu Leu Gly Pro Glu Asn Lys
                725                 730                 735

Leu Val Ala Val Lys Val Leu Asn Leu Leu Lys His Gly Ala Thr Lys
            740                 745                 750

Ser Phe Met Ala Glu Cys Glu Thr Phe Lys Gly Ile Arg His Arg Asn
        755                 760                 765

Leu Val Lys Leu Ile Thr Val Cys Ser Ser Leu Asp Ser Glu Gly Asn
770                 775                 780

Asp Phe Arg Ala Leu Val Tyr Glu Phe Met Pro Lys Gly Ser Leu Asp
785                 790                 795                 800

Met Trp Leu Gln Leu Glu Asp Leu Glu Arg Val Asn Asp His Ser Arg
                805                 810                 815

Ser Leu Thr Pro Ala Glu Lys Leu Asn Ile Ala Ile Asp Val Ala Ser
            820                 825                 830

Ala Leu Glu Tyr Leu His Val His Cys His Asp Pro Val Ala His Cys
        835                 840                 845

Asp Ile Lys Pro Ser Asn Ile Leu Leu Asp Asp Leu Thr Ala His
850                 855                 860

Val Ser Asp Phe Gly Leu Ala Gln Leu Leu Tyr Lys Tyr Asp Arg Glu
```

```
                865                 870                 875                 880
Ser Phe Leu Asn Gln Phe Ser Ser Ala Gly Val Arg Gly Thr Ile Gly
                    885                 890                 895

Tyr Ala Ala Pro Glu Tyr Gly Met Gly Gly Gln Pro Ser Ile Gln Gly
                900                 905                 910

Asp Val Tyr Ser Phe Gly Ile Leu Leu Glu Met Phe Ser Gly Lys
            915                 920                 925

Lys Pro Thr Asp Glu Ser Phe Ala Gly Asp Tyr Asn Leu His Ser Tyr
        930                 935                 940

Thr Lys Ser Ile Leu Ser Gly Cys Thr Ser Gly Gly Ser Asn Ala
945                 950                 955                 960

Ile Asp Glu Gly Leu Arg Leu Val Leu Gln Val Gly Ile Lys Cys Ser
                965                 970                 975

Glu Glu Tyr Pro Arg Asp Arg Met Arg Thr Asp Glu Ala Val Arg Glu
            980                 985                 990

Leu Ile Ser Ile Arg Ser Lys Phe Phe Ser Ser Lys Thr Thr Ile Thr
        995                 1000                1005

Glu Ser Pro Arg Asp Ala Pro Gln Ser Ser Pro Gln Glu Trp Met Leu
    1010                1015                1020

Asn Thr Asp Met His Thr Met
1025                1030

<210> SEQ ID NO 3
<211> LENGTH: 3093
<212> TYPE: DNA
<213> ORGANISM: Arabidopsis thaliana

<400> SEQUENCE: 3
atgaagctgt cctttcact tgttttcaat gctctcacgt tgcttcttca agtttgcatc      60
tttgctcaag ccaggttttc taatgagact gatatgcaag ctttgcttga gttcaagtct     120
caagtttctg aaaacaacaa gagagaggtc ttggcttcat ggaatcactc ctccccattt     180
tgtaattgga ttggagtcac atgtggccgc aggagagaaa gagttataag tttgaacctt     240
ggaggattca gttaaccgg tgtgatctca ccctccattg gtaatctctc ctttcttaga      300
ttacttaatc ttgcagacaa ctcttttgga agtaccatcc ctcaaaaggt gggaaggcta     360
tttaggcttc agtacttgaa catgagctat aatcttctcg aaggaaggat ccgtctagt      420
ctttctaact gctctagact gtcgaccgtt gatttatcgt caaaccatct ggacatggt      480
gttccttcag aactaggttc actttctaag cttgccattc tggatcttag caaaaacaac     540
cttactggaa attttcctgc atctttagga aacttgacgt cacttcagaa gcttgacttt     600
gcatataacc agatgagagg tgagattcca gacgaagtag ctagattgac tcaaatggtg     660
tttttccaaa tagcactgaa tagttttca ggtggttttc ctcctgcatt gtacaacatc     720
tcctctcttg agtctctatc tctagctgac aatagctttt cgggtaatct tagggctgat     780
tttggttatc ttctaccaaa tctaagaaga cttcttttgg gaacaaatca gttcactgga    840
gctattccca aaacacttgc caatatctca agccttgaaa ggtttgatat ctcatctaat    900
tacctgtctg gtagtatccc tttgagcttt ggaaagttac gtaatctgtg gtggttaggg     960
attcgtaata actctcttgg aaataactcg tccagtggtc ttgaatttat tggggctgtg    1020
gcgaactgca ctcaattaga gtacttagat gttggttaca atagacttgg aggtgagctt    1080
cctgcttcta tagccaatct gtccactaca ttgactagtc tgttccttgg acaaaatctt    1140
atctctggaa ccattcctca tgacatcggg aatcttgtaa gcctgcaaga actcagctta    1200
```

```
gaaacaaata tgttgagtgg agaacttccc gtctctttcg ggaagctttt gaacttgcag    1260
gttgtggatc tgtattcaaa tgcaatatcg ggggaaatac catcttattt tggcaacatg    1320
actcggttgc agaagctcca tttgaatagc aatagtttcc acggaagaat ccctcagagt    1380
cttggacgtt gtcgatactt gctagacctg tggatggata caaataggtt gaatgggact    1440
atacctcagg aaatactgca aattccatcc ctcgcttaca tagatttgtc aaacaatttc    1500
ttgacaggcc attttccaga agaagttgga aagttagaac ttcttgttgg actaggtgct    1560
tcgtacaaca aattatcagg aaagatgcca caagctatag ggggttgtct ttcgatggaa    1620
tttctcttta tgcaaggaaa ttcgtttgac ggagccattc cagatataag ccggttggta    1680
agcctaaaga atgttgactt ctccaacaac aatctctctg gccggatacc tcgatatctg    1740
gccagtcttc cttcgctgcg aaatctgaat cttttctatga acaagtttga gggaaggggtg    1800 ccaacaacag gagtgtttcg aaatgctaca gcagtttctg ttttttggtaa cacaaatatt    1860 tgcggaggcg tccgagaaat gcaactaaag ccatgcattg tacaggcatc tccaaggaag    1920
agaaagcctc tgtcagttag aaagaaagtt gtcagtggta tttgtatagg tatagcttcg    1980
cttttgttaa tcataattgt ggcttctctg tgttggttca tgaagaggaa aaagaaaaac    2040
aatgccagtg atggtaaccc atctgattct actactttgg ggatgttcca tgagaaggta    2100
agttatgaag agcttcatag tgcaacaagt cgcttctctt caaccaattt gattggttca    2160
ggcaatttcg gtaatgtgtt taaggattg cttggccctg agaataaact cgtcgcggtt    2220
aaagttttga acctcctaaa gcatggagcg acgaaaagct ttatggcgga atgtgaaacc    2280
ttcaagggta tacgacatcg taaccttgta aaactgataa cggtttgttc aagccttgat    2340
tccgagggaa atgatttcag agctctggtc tatgagttca tgccaaaagg aagtctggat    2400
atgtggctgc agctagaaga tctggaaagg gtaaacgatc actcgagatc tttaacaccc    2460
gcagagaaac tcaacatagc aatagatgtg gcttcagctt tggagtatct gcacgttcat    2520
tgtcatgacc ctgtagctca ctgtgatatt aagccaagca acattcttct agacgatgat    2580
ctgactgctc atgttagtga ctttggtttg gctcagctcc tctataaata cgatcgagaa    2640 tccttttctaa accagtttag ttctgctggt gtcagaggca ccattggcta tgccgcgcca    2700
gagtatggaa tggaggcca accatcaata caaggagatg tgtacagctt cggaattcta    2760
cttttggaga tgtttagtgg aaagaaacca acagatgaat catttgcagg cgattataac    2820
ctccacagct acacaaagtc tatattatcg ggttgcacga gcagtggagg cagcaacgcc    2880
attgatgagg ggttgagact ggttttgcag gtgggggataa agtgttctga agaatatccg    2940
agggatagga tgagaacgga tgaagcagta cgagaattaa tctcaataag atctaagttc    3000
ttcagttcca agacgactat tacagagagt cctcgagatg ctccgcaaag ttctcctcag    3060
gaatggatgt taaatacgga catgcatact atg                                 3093

<210> SEQ ID NO 4
<211> LENGTH: 4563
<212> TYPE: DNA
<213> ORGANISM: Arabidopsis thaliana

<400> SEQUENCE: 4
gactaagaat ggtggaacct gcatcatgta aacatagaat ataatcacaa ttttttatttt     60 gagaagccat tagaattgaa caatgcatgg gttttttgttt attcaaagat gggattttat    120
taagattgac tatatcatac aaaggcttaa acaaaagccc taactttaga tttacaaaag    180
```

-continued

```
cccaagaaag gcccatcaaa taactaactt ttgcagaagc aaatctatct gaacttcatc    240
catggatacg tttccaacaa tacatgggct tgtcacttat aatcgtggct tgtgtcttca    300
aattataagg tcacataaca aaactacatg cagtctattg ttttttctcct tcgtcgacga   360 actactttg ccgtttaata gatcataaac accacacatt tctaccgtca cagtgacaac    420
acttcccaat tattctgatt atggcgcagg ggattcgccg aagatccaa tctgtgctga    480 ttttgcaaga atcgatgggc ttcctcaaat tatcgggcgc ttttttacgac actgcaattg   540 atcgaaacct tcgcaaaaaa tcgtaaagta aaaatcctct ttttatttttt atttaagacc   600 ctttagtagt ttatcaacaa gtaaagattg cattttttttt ggtacatgta atttgtttca   660
gaatttataa acaagaattt ctatcaatgt ctttgaatta actttgataa attcaaactt    720
tctgatggat ggttgtcaat acaagtttca gaagaagatt gaaccaaaa tgactagaca    780 agacgtttgg tgtatgtcga ccaatgtgtt ctgttttggg tagcactttg ccttaactct    840
gtttacacac acacgttat gtgttttgac tgttgaaaaa aaaacgaaag atatttcaaa     900
agtctacgca gtacacaatt tgtttgtttg tgaccatttg caatgatttt ggaccgcatt    960
taattgcccc acgactgtaa tggggatcac agtttggatt ttgcttcttg tttaccttaa   1020 acttccttc attttaatgt tgaagcagaa gaaccttttct tttatcttttt tataatcgac  1080 atgaagctgt ccttttcact tgttttcaat gctctcacgt tgcttcttca agtttgcatc   1140
tttgctcaag ccaggttttc taatgagact gatatgcaag ctttgcttga gttcaagtct  1200
caagtttctg aaaacaacaa gagagaggtc ttggcttcat ggaatcactc ctccccattt   1260
tgtaattgga ttggagtcac atgtggccgc aggagagaaa gagttataag tttgaacctt   1320
ggaggattca agttaaccgg tgtgatctca ccctccattg gtaatctctc ctttcttaga   1380
ttacttaatc ttgcagacaa ctcttttgga agtaccatcc ctcaaaaggt gggaaggcta   1440
tttaggcttc agtacttgaa catgagctat aatcttctcg aaggaaggat tccgtctagt   1500 cttttctaact gctctagact gtcgaccgtt gatttatcgt caaaccatct tggacatggt   1560
gttccttcag aactaggttc actttctaag cttgccattc tggatcttag caaaaacaac   1620
cttactggaa attttcctgc atcttttagga aacttgacgt cacttcagaa gcttgactt   1680 gcatataacc agatgagagg tgagattcca gacgaagtag ctagattgac tcaaatggtg   1740
tttttccaaa tagcactgaa tagttttttca ggtggttttc ctcctgcatt gtacaacatc   1800
tcctctcttg agtctctatc tctagctgac aatagctttt cgggtaatct tagggctgat   1860
tttggttatc ttctaccaaa tctaagaaga cttcttttgg gaacaaatca gttcactgga   1920
gctattccca aaacacttgc caatatctca agccttgaaa ggtttgatat ctcatctaat   1980
tacctgtctg gtagtatccc tttgagcttt ggaaagttac gtaatctgtg gtggttaggg   2040
attcgtaata actctcttgg aaataactcg tccagtggtc ttgaatttat tggggctgtg   2100
gcgaactgca ctcaattaga gtacttagat gttggttaca atagcttgg aggtgagctt    2160 cctgcttcta tagccaatct gtccactaca ttgactagtc tgttccttgg acaaaatctt   2220
atctctggaa ccattcctca tgacatcggg aatcttgtaa gcctgcaaga actcagctta   2280
gaaacaaata tgttgagtgg agaacttccc gtctctttcg ggaagctttt gaacttgcag   2340
gttgtggatc tgtattcaaa tgcaatatcg ggggaaatac catcttattt tggcaacatg   2400
actcggttgc agaagctcca tttgaatagc aatagtttcc acggaagaat ccctcagagt   2460 cttgacgtt gtcgatactt gctagacctg tggatggata caaataggtt gaatgggact    2520
atacctcagg aaatactgca aattccatcc ctcgcttaca tagatttgtc aaacaatttc   2580
```

| | | |
|---|---|---|
| ttgacaggcc attttccaga agaagttgga aagttagaac ttcttgttgg actaggtgct | 2640 |
| tcgtacaaca aattatcagg aaagatgcca caagctatag gggggttgtct ttcgatggaa | 2700 |
| tttctctttta tgcaaggaaa ttcgtttgac ggagccattc cagatataag ccggttggta | 2760 |
| agcctaaaga atgttgactt ctccaacaac aatctctctg gccggatacc tcgatatctg | 2820 |
| gccagtcttc cttcgctgcg aaatctgaat cttttctatga acaagtttga gggaagggtg | 2880 |
| ccaacaacag gagtgtttcg aaatgctaca gcagttctg ttttttggtaa cacaaatatt | 2940 |
| tgcggaggcg tccgagaaat gcaactaaag ccatgcattg tacaggcatc tccaaggaag | 3000 |
| agaaagcctc tgtcagttag aaagaaagtt gtcagtggta tttgtatagg tatagcttcg | 3060 |
| cttttgttaa tcataattgt ggcttctctg tgttggttca tgaagaggaa aaagaaaaac | 3120 |
| aatgccagtg atggtaaccc atctgattct actactttgg ggatgttcca tgagaaggta | 3180 |
| agttatgaag agcttcatag tgcaacaagt cgcttctctt caaccaattt gattggttca | 3240 |
| ggcaatttcg gtaatgtgtt taaaggattg cttggccctg agaataaact cgtcgcggtt | 3300 |
| aaagttttga acctcctaaa gcatggagcg acgaaaagct ttatggcgga atgtgaaacc | 3360 |
| ttcaagggta tacgcatcg taaccttgta aaactgataa cggtttgttc aagccttgat | 3420 |
| tccgagggaa atgatttcag agctctggtc tatgagttca tgccaaaagg aagtctggat | 3480 |
| atgtggctgc agctagaaga tctggaaagg gtaaacgatc actcgagatc tttaacaccc | 3540 |
| gcagagaaac tcaacatagc aatagatgtg gcttcagctt tggagtatct gcacgttcat | 3600 |
| tgtcatgacc ctgtagctca ctgtgatatt aagccaagca acattcttct agacgatgat | 3660 |
| ctgactgctc atgttagtga ctttggtttg gctcagctcc tctataaata cgatcgagaa | 3720 |
| tcctttctaa accagtttag ttctgctggt gtcagaggca ccattggcta tgccgcgcca | 3780 |
| ggttaataaa catctatatg caaaaagtat tgtttaacaa aagagttatc caacctcatt | 3840 |
| gtgtgttgtt tctttgaaat atgtgcagag tatggaatgg gaggccaacc atcaatacaa | 3900 |
| ggagatgtgt acagcttcgg aattctactt ttggagatgt ttagtggaaa gaaaccaaca | 3960 |
| gatgaatcat ttgcaggcga ttataacctc cacagctaca caaagtctat attatcgggt | 4020 |
| tgcacgagca gtggaggcag caacgccatt gatgaggggt tgagactggt tttgcaggtg | 4080 |
| gggataaagt gttctgaaga atatccgagg gataggatga gaacggatga agcagtacga | 4140 |
| gaattaatct caataagatc taagttcttc agttccaaga cgactattac agagagtcct | 4200 |
| cgagatgctc cgcaaagttc tcctcaggaa tggatgttaa atacggacat gcatactatg | 4260 |
| tagacccttc tcaactactt atggggacac agtaaaagtg tatttgcgtg tgcatcatcg | 4320 |
| aaacagaaca atgttgggaa ggaggagaga ctactagtta taataagaga ataaattaaa | 4380 |
| atctatctct gctgtagcct tttttttttt gttgtgggtg aaaatgatta tgatcacata | 4440 |
| tatatggtcg ttgaatatcc ttttttcattt cactttttgat acacgttaaa gttctctgtg | 4500 |
| tccataaaga ttggagaaac cttgtttgaa aatgttcact agtagcaaaa cttacttaac | 4560 |
| aaa | 4563 |

<210> SEQ ID NO 5
<211> LENGTH: 1080
<212> TYPE: DNA
<213> ORGANISM: Arabidopsis thaliana

<400> SEQUENCE: 5
gactaagaat ggtggaacct gcatcatgta aacatagaat ataatcacaa ttttttatttt        60

-continued

```
gagaagccat tagaattgaa caatgcatgg gttttttgttt attcaaagat gggattttat    120
taagattgac tatatcatac aaaggcttaa acaaaagccc taactttaga tttacaaaag    180
cccaagaaag gcccatcaaa taactaactt ttgcagaagc aaatctatct gaacttcatc    240
catggatacg tttccaacaa tacatgggct tgtcacttat aatcgtggct tgtgtcttca    300
aattataagg tcacataaca aaactacatg cagtctattg ttttttctcct tcgtcgacga    360 actactttg ccgtttaata gatcataaac accacacatt tctaccgtca cagtgacaac    420
acttcccaat tattctgatt atggcgcagg ggattcgccg gaagatccaa tctgtgctga    480
ttttgcaaga atcgatgggc ttcctcaaat tatcgggcgc ttttacgac actgcaattg    540 atcgaaacct tcgcaaaaaa tcgtaaagta aaaatcctct ttttattttt atttaagacc    600
ctttagtagt ttatcaacaa gtaaagattg cattttttttt ggtacatgta atttgtttca    660
gaatttataa acaagaattt ctatcaatgt ctttgaatta actttgataa attcaaactt    720
tctgatggat ggttgtcaat acaagtttca gaagaagatt gaaaccaaaa tgactagaca    780
agacgtttgg tgtatgtcga ccaatgtgtt ctgttttggg tagcactttg ccttaactct    840
gtttacacac acacgtttat gtgttttgac tgttgaaaaa aaaacgaaag atatttcaaa    900
agtctacgca gtacacaatt tgtttgtttg tgaccatttg caatgatttt ggaccgcatt    960
taattgcccc acgactgtaa tggggatcac agtttggatt tgcttcttg tttaccttaa    1020 acttcctttc attttaatgt tgaagcagaa gaaccttct tttatctttt tataatcgac    1080
```

<210> SEQ ID NO 6
<211> LENGTH: 18
<212> TYPE: PRT
<213> ORGANISM: Xanthomonas campestris pv. campestris 8004

<400> SEQUENCE: 6

Met Ala Arg Ala Lys Phe Leu Arg Glu Lys Leu His Val Asn Val Gly
1               5                   10                  15

Thr Ile

<210> SEQ ID NO 7
<211> LENGTH: 18
<212> TYPE: PRT
<213> ORGANISM: Xanthomonas campestris pv. musacearum

<400> SEQUENCE: 7

Met Ala Lys Ala Lys Phe Glu Arg Thr Lys Pro His Val Asn Val Gly
1               5                   10                  15

Thr Ile

<210> SEQ ID NO 8
<211> LENGTH: 18
<212> TYPE: PRT
<213> ORGANISM: Ralstonia solanacearum

<400> SEQUENCE: 8

Met Ala Lys Glu Lys Phe Glu Arg Thr Lys Pro His Val Asn Val Gly
1               5                   10                  15

Thr Ile

<210> SEQ ID NO 9
<211> LENGTH: 18
<212> TYPE: PRT
<213> ORGANISM: Pseudomonas syringae pv. tomato DC3000

```
<400> SEQUENCE: 9

Met Ala Lys Glu Lys Phe Asp Arg Ser Leu Pro His Cys Asn Val Gly
 1               5                  10                  15

Thr Ile

<210> SEQ ID NO 10
<211> LENGTH: 18
<212> TYPE: PRT
<213> ORGANISM: Pseudomonas syringae pv. phaseolicola 1448a

<400> SEQUENCE: 10

Met Ala Lys Glu Lys Phe Asp Arg Ser Leu Pro His Val Asn Val Gly
 1               5                  10                  15

Thr Ile

<210> SEQ ID NO 11
<211> LENGTH: 18
<212> TYPE: PRT
<213> ORGANISM: Pseudomonas fluorescens Pf-5

<400> SEQUENCE: 11

Met Ala Lys Glu Lys Phe Glu Arg Asn Lys Pro His Val Asn Val Gly
 1               5                  10                  15

Thr Ile

<210> SEQ ID NO 12
<211> LENGTH: 18
<212> TYPE: PRT
<213> ORGANISM: Pectobacterium atrosepticum

<400> SEQUENCE: 12

Met Ser Lys Glu Lys Phe Glu Arg Thr Lys Pro His Val Asn Val Gly
 1               5                  10                  15

Thr Ile

<210> SEQ ID NO 13
<211> LENGTH: 18
<212> TYPE: PRT
<213> ORGANISM: Candidatus Liberibacter asiaticus str. Psy62

<400> SEQUENCE: 13

Met Val Glu Lys Arg Tyr Val Arg Asn Lys Glu Ser Leu Gly Leu Ser
 1               5                  10                  15

Thr Ile
```

METHODS OF ENHANCING THE RESISTANCE OF PLANTS TO BACTERIAL PATHOGENS

CROSS-REFERENCE TO RELATED APPLICATIONS

This application claims the benefit of U.S. Provisional Patent Application No. 61/110,618, filed Nov. 3, 2008, and U.S. Provisional Application No. 61/187,505, filed Jun. 16, 2009; both of which are hereby incorporated herein in their entirety by reference.

FIELD OF THE INVENTION

This invention relates to the field of agricultural biotechnology, particularly to methods for enhancing the resistance of plants to bacterial pathogens.

BACKGROUND OF THE INVENTION

Plants are under constant attack from a range of pathogens, yet disease symptoms are comparatively rare. Cell-autonomous innate immunity ensures each plant cell has the ability to respond to pathogen attack. In contrast, animals use a circulatory system to ensure full spatial coverage of innate immunity, while jawed vertebrates have supplemented this defense through the evolution of an adaptive immune system. Despite the presence of similar innate immunity strategies in plants and animals, the precise epitopes perceived differ. Thus, instead of divergent evolution from a common ancestor, any similarities are likely to be a result of convergent evolution (Zipfel and Felix, G. (2005) *Current Opinion in Plant Biology* 8:353-360; Ausubel (2005) *Nature Immunology* 6:973-979). In plants, innate immunity consists of three main defense systems: physical, local and systemic. Physical defense include the waxy cuticle and rigid cell wall, as well as secondary metabolites and enzymes possessing anti-microbial properties. This defense is partially breached by stomata or through wounding. Recognition at the local level then relies on the specific perception of microbial compounds. Pattern-recognition receptors (PRRs) recognise pathogen-associated molecular patterns (PAMPs), resulting in PAMP-triggered immunity (PTI). Virulent pathogens secrete effectors into the plant cytosol to suppress PTI. However resistance (R) proteins perceive these microbial effectors to prompt effector-triggered immunity (ETI). These defenses may be breached by further pathogen effectors designed to suppress ETI. The 'zig-zag' model summarises these molecular interactions as five phases occurring over the dynamic coevolution between the plant and its pathogens (Jones and Dangl (2006) *Nature* 444:323-328; Chisholm et al. (2006) *Cell* 124: 803-814). In addition, systemic defense responses induced by PAMPs and/or effector proteins prepare naïve tissues for further attack. Together these three facets form an effective defensive network responsible for the phenomenon whereby most plants are resistant to a majority of microbes (Nürnberger et al. (2004) *Immunological Reviews* 198:249-266).

The primary immune response to bacterial invasion that results in PTI begins with the recognition of PAMPs by PPRs. PTI comprises numerous well-characterized responses including increases in calcium, ethylene, reactive oxygen species (ROS) and extracellular pH, activation of mitogen-activated protein kinase (MAPK) cascades and defense gene expression, deposition of callose, and the inhibition of seedling growth (Ma and Berkowitz (2007) *Cellular Microbiology* 9:2571-2585; Chisholm et al. (2006) *Cell* 124:803-814; Nürnberger et al. (2004) *Immunological Reviews* 198:249-266). These responses are common to elicitation by many bacterial PAMPs, as well as those from fungi and oomycetes. Thus PAMPs are conserved microbial feature which indicate generic danger; it is unlikely the signal conveys information that would allow the plant to distinguish between pathogens (Zipfel et al. (2006) *Cell* 125:749-760).

Over recent years, many potential plant PAMPs have been discovered, whereas the corresponding PRRs have been harder to identify. It has become clear that the breadth of perception of individual PAMPs differs dramatically. Out of the bacterial PAMPs, flagellin is recognised by most plant species whereas responses to elongation factor-Tu (EF-Tu) and the cold-shock protein CSP are restricted to the families Brassicaceae and Solanaceae respectively (Zipfel and Felix, G. (2005) *Current Opinion in Plant Biology* 8:353-360). This difference in perception is indicative of divergent evolution between plant families. An evolutionary arms race occurs whereby the bacterial PAMP evolves to avoid recognition while the plant PRR counter-evolves to increase sensitivity. However plants can perceive multiple PAMPs per microbe. The plant model *Arabidopsis thaliana* (At), for example, can perceive the bacterial PAMPs flagellin, EF-Tu, lipopolysaccharides (LPS) and peptidoglycans (PGN), as well as the fungal PAMPs chitin octamers and ethylene-inducing xylanase (EIX). However the *Arabidopsis thaliana* receptors responsible for this recognition have so far only been identified for flagellin and EF-Tu. In tomato, the receptor LeEIX1/2 perceives chitin, while the rice receptor CEBiP recognises EIX (Kaku et al. (2006) *Proc Natl Acad Sci USA* 103:11086-1109; Ron and Avni (2004) *Plant Cell* 16:1604-1615). But although clear homologues exist in At, their role is not proven. However the receptor-like kinase, CERK1 (also known as LysM RLK1) is essential for chitin elicitor signaling in *Arabidopsis thaliana* (Miya et al. (2007) *Proc Natl Acad Sci USA* 104:19613-19618; Wan et al. (2008) Plant Cell 20:471-381). Meanwhile plant receptors for LPS and PGN are still entirely unknown. (Newman et al. (2007) *Journal of Endotoxin Research* 13:69-84; Gust et al. (2007) *J Biol Chem* 282:32338-48).

Despite the overall effectiveness of innate immunity, plant diseases are still a major social and economic problem. There is a distinct need for effective and stable disease control methods, particularly for Proteobacteria which include the *Pseudomonas* and *Xanthomonas* genera. Bacteria of this phylum have a broad host range in which they cause diverse symptoms affecting both crop yield and quality (Abramovitch et al. (2006) *Nature Reviews Molecular Cell Biology* 7:601-611). There are three main methods of human intervention. (i) Traditional approaches include: removing sources of infection; avoiding and controlling vectors by altering the time of sowing and using chemical sprays; and by breeding for increased resistance. (ii) Biotechnological approaches include producing pathogen-free seed and using biological control methods to help prevent epidemics. (iii) The third method of control is through transgenics. This powerful technique can be used to enhance plant immunity through the expression of additional genes. Transgenic plants may express plant-derived proteins such as additional receptors, signalling molecules, or antimicrobial peptides, or they may express pathogen-derived protein such as effectors. This project focuses on the potential for improving disease resistance through the transgenic expression of additional PRRs.

The PRRs FLS2 and EF-Tu receptor (EFR) are remarkable for two reasons: so far they are the only PRRs found in *Arabidopsis thaliana* and they are the only known PRRs for bacterial PAMPs (Zipfel et al. (2004) *Nature* 428: 764-767; Zipfel et al. (2006) *Cell* 125:749-760). Both belong to the leucine-rich repeat receptor-like kinase (LRR-RLK) family containing members which possess a common domain structure. The LRR region is known to be a key protein recognition motif in a vast variety of protein families (Kobe and Kajava (2001) *Curr. Opin. Struct. Biol.* 11:725-732). In PRR genes, the LRR domain is extracellular and is thought to provide the structural framework that mediates crucial protein-protein interactions. For example, the LRR in FLS2 contains residues essential for flg22 binding, enabling perception of flagellin (Chinchilla et al. (2006) *The Plant Cell* 18:465-476; Dunning et al. (2007) *The Plant Cell* 19:3297-3313). The LRR domain contains tandem copies of a LRR repeat. One LRR repeat is 20-29 residues long and contains the conserved 11-amino acid motif: LxxLxLxxN/CxL, where x can be any amino acid and L can be substituted for other hydrophobic residues in more irregular repeats (Kobe and Kajava (2001) *Curr. Opin. Struct. Biol.* 11:725-732). The LRR repeats are arranged so all secondary structures are parallel to a common axis, resulting in a horseshoe shape. Members of this family also contain a single-pass transmembrane domain and an intracellular Ser/Thr kinase domain which is related to Pelle in *Drosophila* (Shiu et al. (2001) *Proc Natl Acad Sci USA* 98:10763-10768). Interestingly, this is the same structure as class IV R genes such as Xa21 present in rice (Song et al. (1995) *Science* 270:1804-1806). This implies that R genes are adapted from more ancient PRR genes. Thus it would appear that events in the 'zig-zag' model occur in the order they evolved (Nürnberger et al. (2004) *Immunological Reviews* 198:249-266).

Recently, the EF-Tu receptor (EFR) was identified in *Arabidopsis* (Zipfel et al. (2006) Cell 125:749-760). EFR is a receptor kinase that is responsible for perception of EF-Tu. EFR recognizes a region of 18 amino-acids at the N-acetylated terminus of eubacterial EF-Tu that is highly conserved (Kunze et al. (2004) *The Plant Cell* 16:3496-3507; Zipfel et al. (2006) Cell 125:749-760). Notably eubacterial EF-Tu is different than the EF-Tu that are present in plant mitochondria and plastids, thus restricting EFR to only recognising 'non-self'. Previous transient expression of AtEFR in *Nicotiana benthamiana* (Nb) showed that EFR is sufficient for EF-Tu responsiveness and that signalling components downstream of PRRs are conserved across plant families (Zipfel et al. (2006) Cell 125:749-760). However, it was unknown whether the stable expression of EFR confers recognition of EF-Tu epitope elf18 on a transformed plants and triggers activation of basal immune responses therein. It was also unknown whether this transformed plants that stably express EFR can also recognise EF-Tu present in whole pathogenic bacteria leading to enhanced disease resistance to bacterial pathogens.

SUMMARY OF THE INVENTION

Methods are provided for enhancing the resistance of plants to bacterial pathogens. The methods involve transforming a plant cell with a polynucleotide construct comprising a nucleotide sequence that encodes an EF-Tu receptor (EFR). The polynucleotide construct further comprises a promoter that drives expression in the plant and that is operably linked to the nucleotide sequence encoding EFR. The methods further involve regenerating a transformed plant from the transformed plant cell. The transformed plant of the present invention displays enhanced resistance to at least one bacterial pathogen.

Additionally provided are expression cassettes, plants, plant parts, seeds, plant cells and other non-human host cells that are produced by the methods of the present invention.

BRIEF DESCRIPTION OF THE DRAWINGS

FIG. 7. Amino acid sequences of Elf18 peptides from diverse phytopathogenic bacteria.

FIG. 8. Elf18 peptides from diverse phytopathogenic bacteria are active as PAMPs.

FIG. 9. Transgenic EFR tomato (*Solanum lycopersicum* cv. Moneymaker) plants are more resistant to bacterial wilt caused by *Ralstonia solanacearum* GMI1000.

SEQUENCE LISTING

Figure 1:
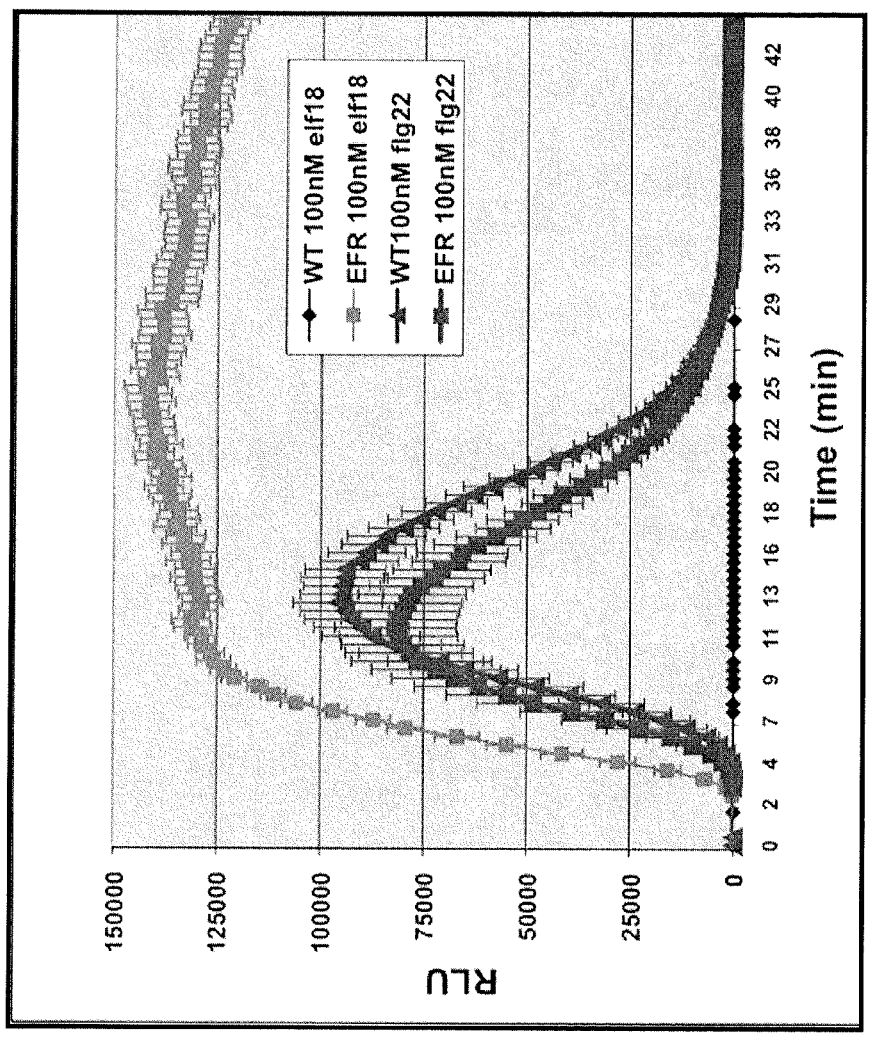
FIG. 1. Production of an oxidative burst in wild-type and EFR transgenic *N. benthamiana*. The peak of luminescence corresponds to the release of reactive oxygen species in response to 100 nM elf18 or flg22 in wild-type or EFR (#18) Nb plants. Values are an average±SE (n=12).

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the full-length coding sequence of the AtEFR gene. The coding sequence of the AtEFR gene corresponds to Accession No. NM_122055.

SEQ ID NO: 2 sets forth the AtEFR amino acid sequence that is encoded by SEQ ID NO: 1.

SEQ ID NO: 3 sets forth the full-length coding sequence of the AtEFR gene minus the stop codon. Nucleotides 1-3093 of SEQ ID NO: 3 correspond to nucleotides 1-3093 of SEQ ID NO: 1. If desired, a stop codon can be added to the 3' end of the nucleotide sequence of SEQ ID NO: 3 or any other coding sequence that lacks a stop codon. Such stop codons include, for example, TAA, TAG, and TGA.

SEQ ID NO: 4 sets forth the genomic sequence of the AtEFR gene. The AtEFR gene corresponds to locus At5g20480 of the *Arabidopsis* genome. The start codon begins at nucleotide 1081 of SEQ ID NO: 4.

SEQ ID NO: 5 sets forth the nucleotide sequence of the AtEFR promoter. Nucleotides 1-1080 of SEQ ID NO: 5 correspond to nucleotides 1-1080 of SEQ ID NO: 4.

SEQ ID NO: 6 sets forth the amino acid sequence of EF-Tu epitope elf18 from *Xanthomonas campestris* pv. *campestris* 8004 and *Xanthomonas campestris* pv. *campestris* B100.

SEQ ID NO: 7 sets forth the amino acid sequence of EF-Tu epitope elf18 from *Xanthomonas campestris* pv. *musacearum*, *Xanthomonas axononpodis* pv. *citri*, *Xanthomonas campestris* pv. *vesicatoria* 85-10, and *Xanthomonas oryzae* pv. *oryzae* MAFF311018.

SEQ ID NO: 8 sets forth the amino acid sequence of EF-Tu epitope elf18 from *Ralstonia solanacearum*.

SEQ ID NO: 9 sets forth the amino acid sequence of EF-Tu epitope elf18 from *Pseudomonas syringae* pv. *tomato* DC3000.

SEQ ID NO: 10 sets forth the amino acid sequence of EF-Tu epitope elf18 from *Pseudomonas syringae* pv. *phaseolicola* 1448a, *Pseudomonas syringae* pv. *syringae* B728a, and *Pseudomonas fluorescens* ND-1.

SEQ ID NO: 11 sets forth the amino acid sequence of EF-Tu epitope elf18 from *Pseudomonas fluorescens* Pf-5.

SEQ ID NO: 12 sets forth the amino acid sequence of EF-Tu epitope elf18 from *Pectobacterium atrosepticum* and *Dickeya*.

SEQ ID NO: 13 sets forth the amino acid sequence of EF-Tu epitope elf18 from *Candidatus Liberibacter asiaticus* str. Psy62.

DETAILED DESCRIPTION OF THE INVENTION

The present invention is based on the discovery that transgenic expression of a Brassicaceae EFR gene in *Nicotiana benthamiana*, a Solanaceous plant, enhances the resistance of the plant to bacterial pathogens. EFR is a pattern-recognition receptor (PRR) that binds specifically with eubacterial EF-Tu, and it is this binding in vivo is that is believed to result in a number of defense responses that are associated with PAMP-triggered immunity (PTI). Because eubacterial EF-Tu is not known to cause PTI in plants outside of the Brassicaceae family, the discovery that the transgenic expression of a Brassicaceae EFR in a non-Brassicaceae plant causes PTI was surprising. Although the present invention is not bound by any particular biological mechanism, the Brassicaceae EFR likely causes PTI by a biological mechanism in non-Brassicaceae plants that is similar to the biological mechanism of Brassicaceae plants.

The methods of the present invention find use in agriculture, particularly in the development of crop plants with enhanced resistance to plant diseases. Such crop plants include resistant and susceptible plant varieties. Such resistant plant varieties may, for example, comprise one or more R genes that are introduced into the plant varieties by conventional plant breeding methods and/or via transformation involving recombinant DNA.

The present invention provides methods for enhancing the resistance of plants to bacterial pathogens. The methods involve transforming a plant cell with a polynucleotide construct comprising a nucleotide sequence that encodes a eubacterial EF-Tu receptor (EFR) and regenerating a transformed plant therefrom. As disclosed herein below, the domain of EF-Tu that interacts with EFR to initiate PTI is highly conserved across eubacterial EF-Tu proteins. Therefore, the methods of the present invention are expected to enhance a resistance of a plant to more than just one or two bacterial pathogens.

In a preferred embodiment of the invention, the nucleotide sequence that encodes an EFR is a nucleotide sequence that encodes the EFR referred to herein as AtEFR, which is the EFR that corresponds to locus At5g20480 of the *Arabidopsis* genome. Nucleotide sequences encoding AtEFR include, but are not limited to, the nucleotide sequences set forth in SEQ ID NO: 1, 3, and 4, and a nucleotide sequence encoding the amino acid sequence set forth in SEQ ID NO: 2.

In other embodiments, the nucleotide sequence encoding an EFR homolog is selected from the group consisting of the coding sequences that correspond to loci AT3G47110, AT5G39390, AT3G47580, AT3G47570, AT3G47090, and AT2G24130 of the *Arabidopsis* genome. The loci of the *Arabidopsis* genome and the corresponding amino acid sequences can be found at The *Arabidopsis* Information Resource (TAIR) (on the World Wide Web at arabidopsis.org) and GenBank (on the World Wide Web at ncbi.nlm.nih.gov/Genbank/).

Preferably, the methods of the present invention enhance the resistance of a plant to one or more eubacterial pathogens. More preferably, the methods of the present invention enhance the resistance of a plant to two, three, four, five, or more eubacterial pathogens. Most preferably, the methods of the present invention enhance the resistance of a plant to all eubacterial pathogens that can cause disease symptoms on a like plant that has not been enhanced by the methods disclosed herein. Such a "like plant" is the same species a plant of the invention that has been enhanced for disease resistance by the methods disclosed herein. Preferably, such a "like plant" is the same variety or cultivar as the enhanced plant of the invention.

Unless stated otherwise or apparent from the context, "eubacterial pathogens" are plant pathogens that are "eubacteria", which are also known as "true bacteria". It is recognized that "eubacteria" refers to all bacteria except for archaebacteria.

In the methods of the present invention, the polynucleotide construct further comprises a promoter that drives expression in the plant and that is operably linked to the nucleotide sequence encoding EFR. The present invention does not depend on a particular promoter. The promoter can be the native EFR promoter or a promoter from another plant or non-plant gene that is capable of driving expression of the operably linked EFR coding sequences in the plant of interest at the desired time and location in the plant. Such promoters include, but are not limited to, constitutive promoters, pathogen-inducible promoters, tissue-preferred promoters, and chemical-regulated promoters.

For expression of the EFR protein in a plant or plant cells, the methods of the invention involve transforming a plant with a polynucleotide construct of the present invention that comprises a nucleotide sequence encoding the EFR protein. Such a nucleotide sequence can be operably linked to a promoter that drives expression in a plant cell. The present invention does not depend on a particular promoter. The promoter can be the native EFR promoter or a promoter from another plant or non-plant gene that is capable of driving expression of the operably linked EFR coding sequences in the plant of interest at the desired time and location in the plant. Any promoter known in the art can be used in the methods of the invention including, but not limited to, the native EFR promoter, constitutive promoters, pathogen-inducible promoters, wound-inducible promoters, tissue-preferred promoters, and chemical-regulated promoters. The choice of promoter will depend on the desired timing and location of expression in the transformed plant or other factors. In one embodiment of the invention, the native AtEFR promoter—either in its native genomic linkage to the downstream AtEFR gene sequences or as part of a recombinant nucleic acid molecule further comprising a AtEFR coding sequence—is employed to express the EFR protein in a plant. In a preferred embodiment of the invention, the promoter is the AtEFR promoter comprising the nucleotide sequence set forth in SEQ ID NO: 5.

The methods for enhancing the resistance of a plant to at least one bacterial pathogen find use in the development of improved crop, fruit, and ornamental plant varieties. Such plant varieties will display enhanced resistance to one or more bacterial pathogens, thereby reducing the need for the application of potentially harmful chemical pesticides when compared to similar plant varieties that have not been enhanced by the methods disclosed herein.

In other embodiments, the methods can involve additional R genes to increase plant resistance to a single plant pathogen or increase plant resistant to different plant pathogen. Such genes typically encode proteins containing leucine-rich repeats (LRRs). Such R proteins can contain transmembrane domains, or can be localized intracellularly. In addition, many R proteins contain nucleotide-binding (NB) domains (also referred to as P-loops), Toll-interleukin-1 receptor (TIR) domains, or protein kinase domains in various combinations. R genes have been isolated from a wide range of plant species, including *Arabidopsis*, flax, maize, rice, wheat, soybean, tomato, potato, and others (reviewed in, for example: Ellis et al. (2000) *Curr. Opin. Plant Biol.* 3:278-84; Jones and Dangl (2006) *Nature* 444:323-29; Bent and Mackey (2007) *Annu. Rev. Phytopathol.* 45:399-436; Tameling and Takken (2008) *Eur. J. Plant Pathol.* 121:243-255. In one embodiment of the invention, a pepper plant comprising at least one Bs2 resistance gene, at least one Bs3 resistance gene, or at least one Bs2 resistance gene and at least one Bs3 resistance gene is used in the methods disclosed herein. The nucleotide sequences of Bs2 and Bs3 have been previously disclosed. See, U.S. Pat. Nos. 6,262,343 and 6,762,285, (Tai et al. (1999) *Proc Natl. Acad. Sci. USA* 96:14153-14158), and Römer et al. (2007) *Science* 318:645-648; each of which is herein incorporated by reference.

The invention encompasses the use of isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed EFR polynucleotides and proteins encoded thereby are also encompassed by the present invention. By "fragment" is intended a portion of the polynucleotide or a portion of the amino acid sequence and hence protein encoded thereby. Fragments of a polynucleotides comprising coding sequences may encode protein fragments that retain biological activity of the native protein and hence EFR activity. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

A fragment of an EFR polynucleotide that encodes a biologically active portion of an EFR protein of the invention will encode at least 15, 25, 30, 50, 100, 150, 200, 250, or 300 contiguous amino acids, or up to the total number of amino acids present in a full-length EFR protein of the invention (for example, 1031 amino acids for SEQ ID NO: 2). Fragments of an EFR polynucleotide that are useful as hybridization probes or PCR primers generally need not encode a biologically active portion of an EFR protein or EFR promoter.

Thus, a fragment of an EFR polynucleotide may encode a biologically active portion of an EFR protein or an EFR promoter, or it may be a fragment that can be used as a hybridization probe or PCR primer using methods disclosed below. A biologically active portion of an EFR protein can be prepared by isolating a portion of one of the an EFR polynucleotides of the invention, expressing the encoded portion of the an EFR protein (e.g., by recombinant expression in vivo), and assessing the activity of the encoded portion of the EFR protein. Polynucleotides that are fragments of an EFR nucleotide sequence comprise at least 16, 20, 50, 75, 100, 150, 200, 250, 300, 350, 400, 450, 500, 550, 600, 650, 700, 800, 900, 1000, 1100, 1200, 1300, 1400, 1500, 2000, 2500, or 3000 contiguous nucleotides, or up to the number of nucleotides present in a full-length EFR polynucleotide disclosed herein (for example, 3096, 3093, and 4563 nucleotides for SEQ ID NO: 1, 3, and 4, respectively).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the EFR polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an EFR protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, that is, they sense the presence of a bacterial EF-Tu peptide and trigger plant disease resistance responses as described herein. The biological activity of variant proteins of the invention can be assayed, for example, by *Agrobacterium*-mediated transient expression in *Nicotiana benthamiana* followed by measurement of the oxidative burst triggered by elf18, as described in Zipfel et al. (2006) *Cell* 125:749-760. This same assay can also be conducted using *Arabidopsis thaliana* efr-1 leaves instead of *Nicotiana benthamiana* leaves. Such variants may result from, for example, genetic polymorphism or from human manipulation. Biologically active variants of a native EFR protein of the invention will have at least about 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The biological activity of variant proteins of the invention can be assayed, for example, by *Agrobacterium*-mediated transient expression in *Nicotiana benthamiana* followed by measurement of the oxidative burst triggered by elf18, as described in Zipfel et al. (2006) *Cell* 125:749-760. This same assay can also be conducted using *Arabidopsis thaliana* efr-1 leaves instead of *Nicotiana benthamiana* leaves.

The proteins of the invention may be altered in various ways including amino acid substitutions, deletions, truncations, and insertions. Methods for such manipulations are generally known in the art. For example, amino acid sequence variants and fragments of the EFR proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired EFR biological activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the EFR activity can be evaluated by routine assays as described below.

An EFR is a plant receptor kinase that binds eubacterial EF-Tu. When trigged by EF-Tu, EFR can induce in a plant PAMP responses such as, for example, enhanced binding of ethylene and induction of an oxidative burst in the plant. For the present invention, a polypeptide comprises EFR activity when said polypeptide is capable of binding with an EF-Tu and inducing one or more plant PAMP responses when the EFR is expressed in plant and exposed to an EF-Tu. Preferably, an EFR of the present invention will specifically bind to one or more EF-Tu epitope elf18 selected from the group consisting of the elf18 epitopes having the amino acid sequences set forth SEQ ID NOS: 6-12. In a preferred embodiment the invention, an EFR of the present invention will specifically bind to the EF-Tu epitope elf18 having the amino acid sequence set forth in SEQ ID NO: 6, and optionally bind to one or more additional EF-Tu epitope elf18 selected from the group consisting of the elf18 epitopes having the amino acid sequences set forth SEQ ID NOS: 7-12. See, Example 1 below. See also, Zipfel et al. (2006) *Cell* 125:749-760 and Kunze et al. (2004) *The Plant Cell* 16:3496-3507; both of which are herein incorporated by reference.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire EFR sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an EFR protein and which hybridize under stringent conditions to at least one of the EFR polynucleotides disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also, Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the EFR polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire EFR polynucleotide disclosed herein, or one or more portions thereof, may be used as a probe capable of specifically hybridizing to corresponding EFR polynucleotide and messenger RNAs. To achieve specific hybridization under a variety of conditions, such probes include sequences that are unique among EFR polynucleotide sequences and are optimally at least about 10 nucleotides in length, and most optimally at least about 20 nucleotides in length. Such probes may be used to amplify corresponding EFR polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the methods of the present invention encompass the use of polynucleotide molecules and proteins comprising a nucleotide or an amino acid sequence that is sufficiently identical to the nucleotide sequence of SEQ ID NOS: 1, 3, and/or 4, or to the amino acid sequence of SEQ ID NO: 2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g.,)(BLAST and NBLAST) can be used. See on the World Wide Web: ncbi.nlm.nih.gov. Another preferred, non-limiting example of a mathematical algorithm utilized for the comparison of sequences is the algorithm of Myers and Miller (1988) CABIOS 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the World Wide Web at ebi.ac.uk/Tools/clustalw/index.html).

The use herein of the terms "polynucleotide", "polynucleotide construct", "polynucleotide molecule" is not intended to limit the present invention to polynucleotides, polynucleotide constructs, and polynucleotide molecules comprising DNA. Those of ordinary skill in the art will recognize that polynucleotides, polynucleotide constructs, and polynucleotide molecules can comprise ribonucleotides and combinations of ribonucleotides and deoxyribonucleotides. Such deoxyribonucleotides and ribonucleotides include both naturally occurring molecules and synthetic analogues. The polynucleotides, polynucleotide constructs, and polynucleotide molecules of the invention also encompass all forms of sequences including, but not limited to, single-stranded forms, double-stranded forms, hairpins, stem-and-loop structures, and the like.

The EFR polynucleotides of the invention comprising EFR protein coding sequences can be provided in expression cassettes for expression in the plant or other organism or non-human host cell of interest. The cassette will include 5' and 3' regulatory sequences operably linked to a EFR polynucleotide of the invention. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the EFR polynucleotide to be under the transcriptional regulation of the regulatory regions. The expression cassette may additionally contain selectable marker genes.

By "gene of interest" is intended any nucleotide sequence that can be expressed when operable linked to a promoter. A gene of interest of the present invention may, but need not, encode a protein. Unless stated otherwise or readily apparent from the context, when a gene of interest of the present invention is said to be operably linked to a promoter of the invention, the gene of interest does not by itself comprise a functional promoter.

The expression cassette will include in the 5'-3' direction of transcription, a transcriptional and translational initiation region (i.e., a promoter), a EFR polynucleotide of the invention, and a transcriptional and translational termination region (i.e., termination region) functional in plants or other organism or non-human host cell. The regulatory regions (i.e., promoters, transcriptional regulatory regions, and translational termination regions) and/or the EFR polynucleotide of the invention may be native/analogous to the host cell or to each other. Alternatively, the regulatory regions and/or the EFR polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

While it may be optimal to express the EFR coding sequences using heterologous promoters, the native promoter sequences or truncations described herein below may be used. Such constructs can change expression levels of the EFR protein in the plant or plant cell. Thus, the phenotype of the plant or plant cell can be altered. In one embodiment of the invention, the AtEFR promoter is operably linked to the AtEFR coding sequence.

The termination region may be native with the transcriptional initiation region, may be native with the operably linked EFR polynucleotide of interest, may be native with the plant host, or may be derived from another source (i.e., foreign or heterologous) to the promoter, the EFR polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced EFR expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) Bio/Technol. 10:309-314; Dhir, et al. (1992) *Plant Physiol.* 99:81-88; Casas et al. (1993) *Proc. Nat. Acad Sci. USA* 90:11212-

11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo *Chin Sci. Bull.* 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; Wan, Y. C. and Lemaux, P. G. (1994) *Plant Physiol.* 104: 3748; U.S. Pat. No. 5,792,935 U.S. Pat. No. 6,133,035; May et al. (1995) *Biotechnology* 13:486-492; Dhed'a, et al. (1991) *Fruits* 46:125-135); Sagi, et al. (1995) *Biotechnology* 13:481-485; Marroquin et al. (1993) *In Vivo Cell. Div. Biol.* 29P:43-46; Ma (1991) "Somatic Embryogenesis and Plant Regeneration from Cell Suspension Culture of Banana", in *Proceedings of Symposium on Tissue Culture of Horicultural Crops*, Mar. 8-9, 1988, Department of Horticulture, National Taiwan University, Taipei, Taiwan, pp. 181-188.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.,* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues,* ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the a EFR protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Examples of plant species of interest include, but are not limited to, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), tomatillo (*Physalis philadelphica*), petunia (*Petunia* spp., e.g., *Petunia×hybrida* or *Petunia hybrida*), corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

In a preferred embodiment, the plants of the present invention are members of the Solanaceae family which is commonly known as the Nightshade family. Plants that are members of the Solanaceae family are also referred to herein as Solanaceous plants. Solanaceous plants of the present invention include, but are not limited to, tomato, potato, pepper, tobacco, eggplant, tomatillo, and petunia.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruits, roots, root tips, anthers, and the like. Progeny, variants, and mutants of the regenerated plants are also included within the scope of the invention, provided that these parts comprise the introduced polynucleotides.

The invention is drawn to compositions and methods for enhancing the resistance of a plant to plant disease caused by a bacterial pathogen. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

Pathogens of the invention are bacteria, insects, nematodes, fungi, and the like. The preferred pathogens of the present invention are bacterial pathogens. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium alboatrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmopora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium moniliforme* var. *subglutinans, Erwinia stewartii, F. verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum* turcicum I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia carotovora*, Corn stunt spiroplasma, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *C. sublineolum*, *Cercospora sorghi*, *Gloeocercospora sorghi*, *Ascochyta sorghina*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Perconia circinate*, *Fusarium moniliforme*, *Alternaria alternate*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari*, *Sporisorium reilianum* (*Sphacelotheca reiliana*), *Sphacelotheca cruenta*, *Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.; Tomato: *Corynebacterium michiganense* pv. *michiganense, Pseudomonas syringae* pv. *tomato, Ralstonia solanacearum, Xanthomonas vesicatoria, Xanthomonas perforans, Alternaria solani, Alternaria porri, Collectotrichum* spp., *Fulvia fulva* Syn. *Cladosporium fulvum, Fusarium oxysporum* f. *lycopersici, Leveillula taurica/Oidiopsis taurica, Phytophthora infestans*, other *Phytophthora* spp., *Pseudocercospora fuligena* Syn. *Cercospora fuligena, Sclerotium rolfsii, Septoria lycopersici, Meloidogyne* spp.; Potato: *Ralstonia solanacearum, Pseudomonas solanacearum, Erwinia carotovora* subsp. *Atroseptica Erwinia carotovora* subsp. *Carotovora, Pectobacterium carotovorum* subsp. *Atrosepticum, Pseudomonas fluorescens, Clavibacter michiganensis* subsp. *Sepedonicus, Corynebacterium sepedonicum, Streptomyces scabiei, Colletotrichum coccodes, Alternaria alternate, Mycovellosiella concors, Cercospora solani, Macrophomina phaseolina, Sclerotium bataticola, Choanephora cucurbitarum, Puccinia pittieriana, Aecidium cantensis, Alternaria solani, Fusarium* spp., *Phoma solanicola f. foveata, Botrytis cinerea, Botryotinia fuceliana, Phytophthora infestans, Pythium* spp., *Phoma andigena* var. *andina, Pleospora herbarum, Stemphylium herbarum, Erysiphe cichoracearum, Spongospora subterranean Rhizoctonia solani, Thanatephorus cucumeris, Rosellinia* sp. *Dematophora* sp., *Septoria lycopersici, Helminthosporium solani, Polyscytalum pustulans, Sclerotium rolfsii, Athelia Angiosorus solani, Ulocladium atrum, Verticillium albo-atrum, V. dahlia, Synchytrium endobioticum, Sclerotinia sclerotiorum*; Banana: *Colletotrichum musae, Armillaria mellea, Armillaria tabescens, Pseudomonas solanacearum, Phyllachora musicola, Mycosphaerella fijiensis, Rosellinia bunodes, Pseudomas* spp., *Pestalotiopsis leprogena, Cercospora hayi, Pseudomonas solanacearum, Ceratocystis paradoxa, Verticillium theobromae, Trachysphaera fructigena, Cladosporium musae, Junghuhnia vincta, Cordana johnstonii, Cordana musae, Fusarium pallidoroseum, Colletotrichum musae, Verticillium theobromae, Fusarium* spp *Acremonium* spp., *Cylindrocladium* spp., *Deightoniella torulosa, Nattrassia mangiferae, Dreschslera gigantean, Guignardia musae, Botryosphaeria ribis, Fusarium solani, Nectria haematococca, Fusarium oxysporum, Rhizoctonia* spp., *Colletotrichum musae, Uredo musae, Uromyces musae, Acrodontium simplex, Curvularia eragrostidis, Drechslera musae-sapientum, Leptosphaeria musarum, Pestalotiopsis disseminate, Ceratocystis paradoxa, Haplobasidion musae, Marasmiellus inoderma, Pseudomonas solanacearum, Radopholus similis, Lasiodiplodia theobromae, Fusarium pallidoroseum, Verticillium theobromae, Pestalotiopsis palmarum, Phaeoseptoria musae, Pyricularia grisea, Fusarium moniliforme, Gibberella fujikuroi, Erwinia carotovora, Erwinia chrysanthemi, Cylindrocarpon musae, Meloidogyne arenaria, Meloidogyne incognita, Meloidogyne javanica, Pratylenchus coffeae, Pratylenchus goodeyi, Pratylenchus brachyurus, Pratylenchus reniformia, Sclerotinia sclerotiorum, Nectria foliicola, Mycosphaerella musicola, Pseudocercospora musae, Limacinula tenuis, Mycosphaerella musae, Helicotylenchus multicinctus, Helicotylenchus dihystera, Nigrospora sphaerica, Trachysphaera frutigena, Ramichloridium musae, Verticillium theobromae.*

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those. In addition, genes of interest include genes encoding enzymes and other proteins from plants and other sources including prokaryotes and other eukaryotes.

Example 1

Characterization of Transgenic *Nicotiana benthamiana* (Nb) Stably Expressing AtEFR Although plant defense responses are not altogether understood at a molecular level, they can be used to assay for the ability of a plant to anticipate a microbial attack. In this project, four well-known PTI responses were used to assay for the ability of heterologously expressed AtEFR to confer responsiveness to the EF-Tu epitope elf18. The well-characterized flg22 epitope of flagellin is used as a positive control and water or assay mix is used as a negative control. The use of the epitopes elf18 and flg22 instead of the whole elicitor or pathogen ensures each treatment is one specific elicitor, not several acting together.

Materials and Methods

All experiments used homozygous T4 Nb lines (subsequently referred to as EFR) expressing AtEFRp::EFR as well as wild-type Nb as a negative control. In most cases, treatments used 100 nM elf18 or flg22 diluted in water, MS-10, or the relevant assay mix and were repeated a minimum of three times.

AtEFRp::EFR was constructed as described in Zipfel et al. (2006) *Cell* 125:749-760, which is herein incorporated by reference. A 4.1 kb fragment including EFR (At5g20480) and 1080 bp of upstream sequence was amplified from Col-0 genomic DNA using the Expand High Fidelity System (Roche) and placed upstream to a GFP coding sequence in a pGEM-T Easy plasmid (Promega). After digestion with NotI, a EFRp::EFRfragment was cloned into the binary vector pGREENII/T-0229 (Hellens et al. (2000) *Plant Mol. Biol.* 42:819-832).

Inhibition of Seedling Growth: Fresh Weight Measurement

Wild-type, #16 and #18 Nb as well as Col and efr *Arabidopsis thaliana* seedlings were grown for one week on MS1% sucrose agar plates, then transferred to liquid culture and were grown for one week in a serial dilution or elf18 or flg22. Dilutions of 0.1, 1, 10, 100 and 1000 nM were used for all five plant lines. Seedlings (n=4) were blotted on absorbent paper and their fresh weight was measured.

Oxidative Burst: Luminol-Based Assay

To measure the production of reactive oxygen species (ROS) in leaf tissue, size #1 leaf discs (Nb; n=12, tomato; n=8) were floated overnight in water. Each disc was then transferred to a well containing an assay mix of luminol (200 µM) and peroxidase (20 µg/ml) in 100 µl water. Each well was then treated with either: assay mix, 100 nm elf18, or 100 nm flg22. Luminescence in a 96-well plate was subsequently measured using a Flash Varioskan luminometer.

Early and Late Marker Gene Expression: Analysis by RT-PCR

Wild-type and #18 Nb were grown for one week on agar plates, then transferred to liquid culture and were grown for a further week. The expression of PAMP-induced genes was monitored over a time course. Seedlings were treated with 100 nM elf18 or flg22 for 0, 30, 60 or 180 minutes, and frozen in liquid nitrogen.

In brief: four elicited seedlings were thoroughly ground directly in the supplied extraction buffer in Eppendorf tubes using a pestle on an IKA RW 20 stirrer. Total RNAs were extracted using the Qiagen Rneasy Plant Mini kit. The quality of the extracted RNA was confirmed byrunning an ethidium bromide-stained agarose gel to reveal rRNAs. DNase treatment was performed using TURBO DNA-free kit (Ambion) and the concentration of total RNA was then measured using a Nanodrop. First strand cDNA synthesis was performed using SuperScript II Reverse Transcriptase (Invitrogen) in combination with Oligo(dT) prime on 2 µg of total RNA. One µl of cDNA was used in PCR under the following conditions: 95° C. 2 min; [95° C. 45 sec; 58° C. 45 sec; 55° C. 30 sec; 72° C. 1.5 min]×25; 72° C. 5 min. The genes used as defense markers were: CYP72D2 (cytochrome P450), FLS2 (receptor kinase for flg22), ACRE132 (putative RING finger protein) and WRKY22 (transcription factor). As loading control the constitutively expressed EF-1α housekeeping gene was also amplified.

Callose Deposition: Aniline Blue Staining for Fluorescent Microscopy

A solution of either water, 100 nM elf18, or 100 nM flg22 was used to infiltrate leaves of 4-week old wild-type and EFR Nb. Size #3 leaf discs (n=8) were sampled after ±16 hours and destained in methanol overnight. Discs were rinsed in water, then left to stain overnight in a solution of 0.05% aniline blue in 50 mM phosphate buffer pH 8.5. Callose deposition at the plant cell periphery could then be viewed under a fluorescence microscope.

Infection Assays: Disease Scoring and Growth Curves Following Bacterial Infections Five different bacterial strains were used to inoculate ~4-week old Nb plants: *P. syringae* pv. *syringae* B728a, *P. syringae* pv. *tabaci* 6665, *P. syringae* pv. *tabaci* 11528, *Xanthomonas campestris* pv. *campestris* 8004 and *P. syringae* pv. tomato DC3000. Inoculation was performed either through spraying 1×10⁸ cfu/ml bacteria with 0.06% Silwett L77 over the whole plant (n=2) or through infiltrating 1×10⁵ cfu/ml bacteria into leaves (n=2). Two #1 leaf discs (n=4) were taken over a time course of several days then ground in water using a pestle in IKA RW 20 stirrer. The product was serially diluted, then plated onto TSA plates which were incubated for 24 hours at 28° C. then 12 hours at room temperature to produce visible colonies for counting.

Transient Expression After Agro-Infiltration: Qualitative GUS Assay

*A. tumefaciens* GV3101 carrying pBIN19-35S::GUS-HA was grown overnight in L media with 50 µg/ml Rifampicin and 50 µg/ml Kanamycin. This culture was diluted in 1/10 volume and grown for a further five hours. The cells were spun down and resuspended in water to OD600=0.4. This culture was used to infiltrate patches of Nb leaf. After two days, #8 leaf discs (n=16) were vacuum infiltrated with GUS staining solution and incubated overnight at 37° C. The solution was then replaced with methanol to destain the discs to reveal areas of GUS expression.

Gall Formation After Agro-Inoculation: Disease Scoring

*A. tumefaciens* A281 was plated onto L media with 10 µg/ml Rifampicin and incubated at 28° C. for 2 days. This plate was used to stab inoculate stems from 5 different Nb plants at 3 leaf joints (n=15). The plants were grown for three weeks, and then the resultant crown-galls were excised and weighed.

Transcription of Defense Genes in Native Plants: Analysis by RT-PCR

Wild-type and #18 Nb seedlings were grown for two weeks on sterile agar plates, then transferred to grow for a further four weeks in non-sterile soil. The level of expression of the two Nb PR-1 genes was assayed each week for six weeks. For the first two weeks, approximately 10-20 seedlings were sampled. After transfer to soil, a #6 punch was used to take leaf disc samples (n=4). The same RT-PCR protocol was used, the only differences being that the RNA was eluted in just 30 µl Rnase-free water, then just 0.5 µg RNA was used to make the first strand of cDNA, so to compensate the number of PCR cycles was extended to 32 in order to produce an observable band.

Results

Oxidative Burst

One early aspect of PTI is the rapid production of reactive oxygen species (ROS) to form an oxidative burst within minutes. These molecules have three parallel roles in defense: the ROS are toxic to the pathogen, help catalyse cell wall cross-linking by oxidation, and may also have a role in signalling (Nürnberger et al. (2004) *Immunological Reviews* 198:249-266). FIG. 1 demonstrates that expression of AtEFR confers the ability to perceive and respond to elf18. The plants transgenic for AtEFR exhibited a peak of luminescence corresponding to a burst of ROS released minutes after elf18 treatment. However similar experiments never revealed a burst of ROS in wild-type Nb after elf18 elicitation. The negative control proved this peak was not due to a wounding effect that might have occurred due to pipetting of the assay solution (FIG. 1).

Expression of Early and Late PAMP-Responsive Marker Genes

Figure 2:
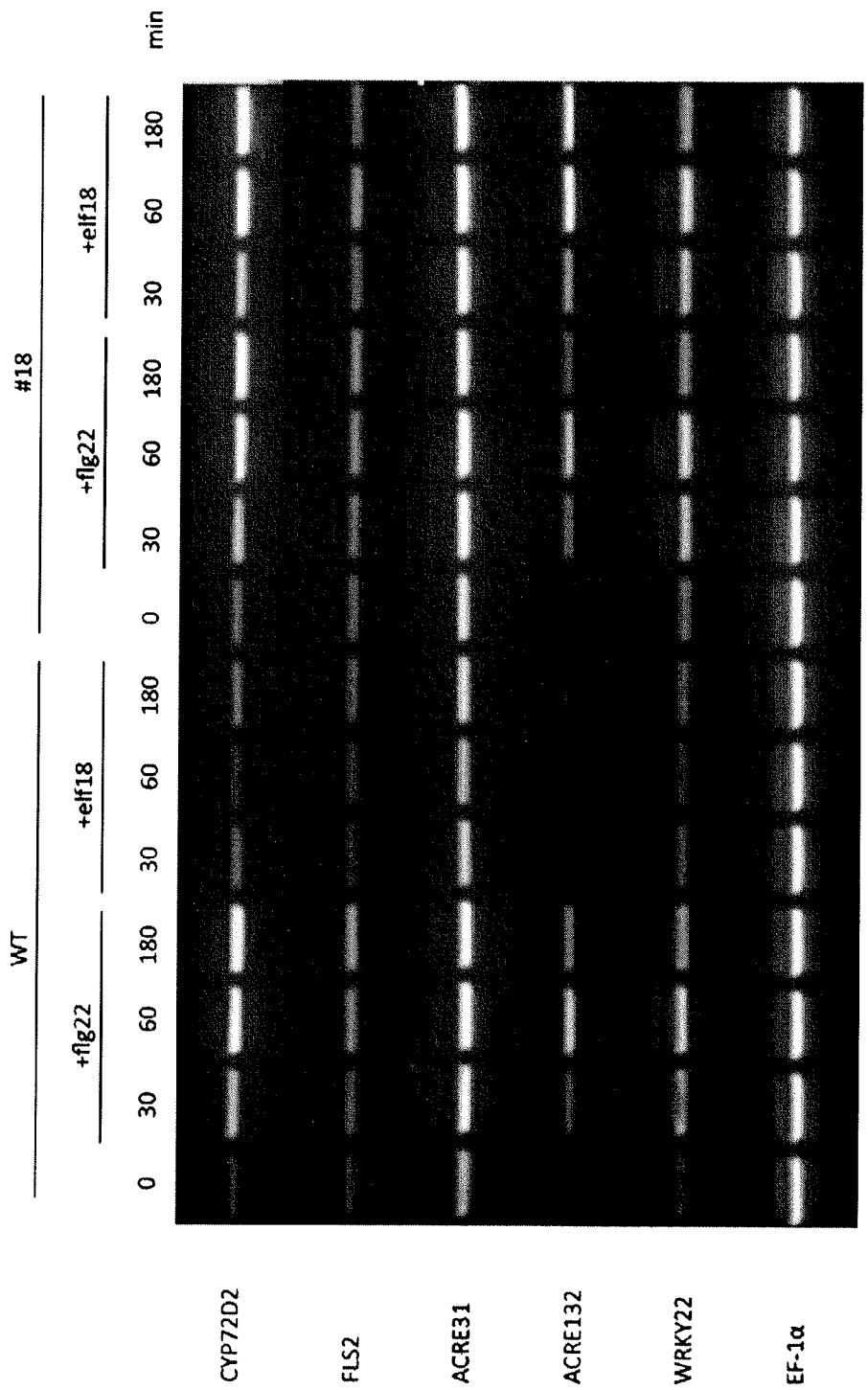
FIG. 2. Expression of early defense marker genes in wild-type and EFR transgenic *N. benthamiana*. RT-PCR reveals the extent of defense marker gene induction at timepoints of 0, 30, 60 and 180 min following elf18 or flg22 treatment. Constitutively expressed EF-1α serves as a loading control.

A number of genes are known to be induced at different timepoints during the transcriptional innate immune response. Early and late defense genes which are activated in response to PAMPs were used in this study. For example, WRKY22 binds W-box DNA elements present in several promoters, to activate transcription of defense-related genes (Asai et al. (2002) *Nature* 415:977-983). Therefore a time course was used to demonstrate the temporal change in emphasis of induction. Clearly, elicitation with flg22 induces the expression of defense markers in both wild-type and EFR plants, whereas elf18 is unable to elicit a significant amount of expression in wild-type plants (FIG. 2). Crucially this trend differs in EFR plants where elf18 treatment results in marker gene expression which is at least as strong as under flg22 treatment (FIG. 2).

Callose Deposition

A much later response is the deposition of callose at the plant cell wall, occurring a couple of hours after elicitation. These deposits are revealed as bright blue specks on a dark blue background after aniline blue staining EFR plants displayed a comparatively a stronger response to elf18 elicitation, relative to wild-type plants (data not shown). However, the positive control of flg22 elicitation did not work well for wild-type plants either (data not shown). In general these results are not as distinctive as is commonly observed in *Arabidopsis* so alternative assays for defense responses are preferable when working with Nb.

Seedling Growth Inhibition

Figure 3A:
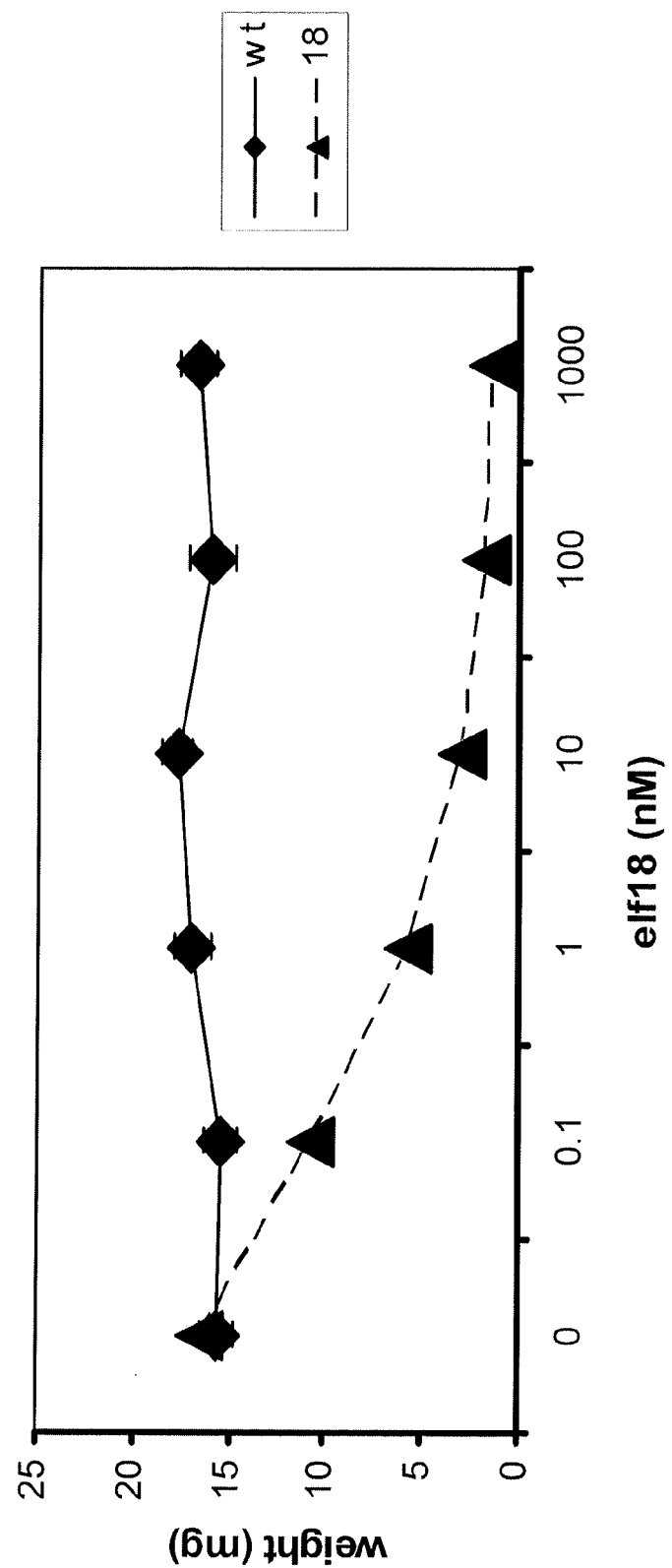
FIG. 3. Seedling growth inhibition in wild-type and EFR transgenic *N. benthamiana*. Seedling fresh weight is measured to detect if growth inhibition has occurred. Nb seedlings are treated with a serial dilution of elf18 (A) or flg22 (C). Likewise *Arabidopsis thaliana* seedlings are treated with the same dilutions of elf18 (B) or flg22 (D). Results shown correspond to an average±SE (n=8).
Figure 3B:
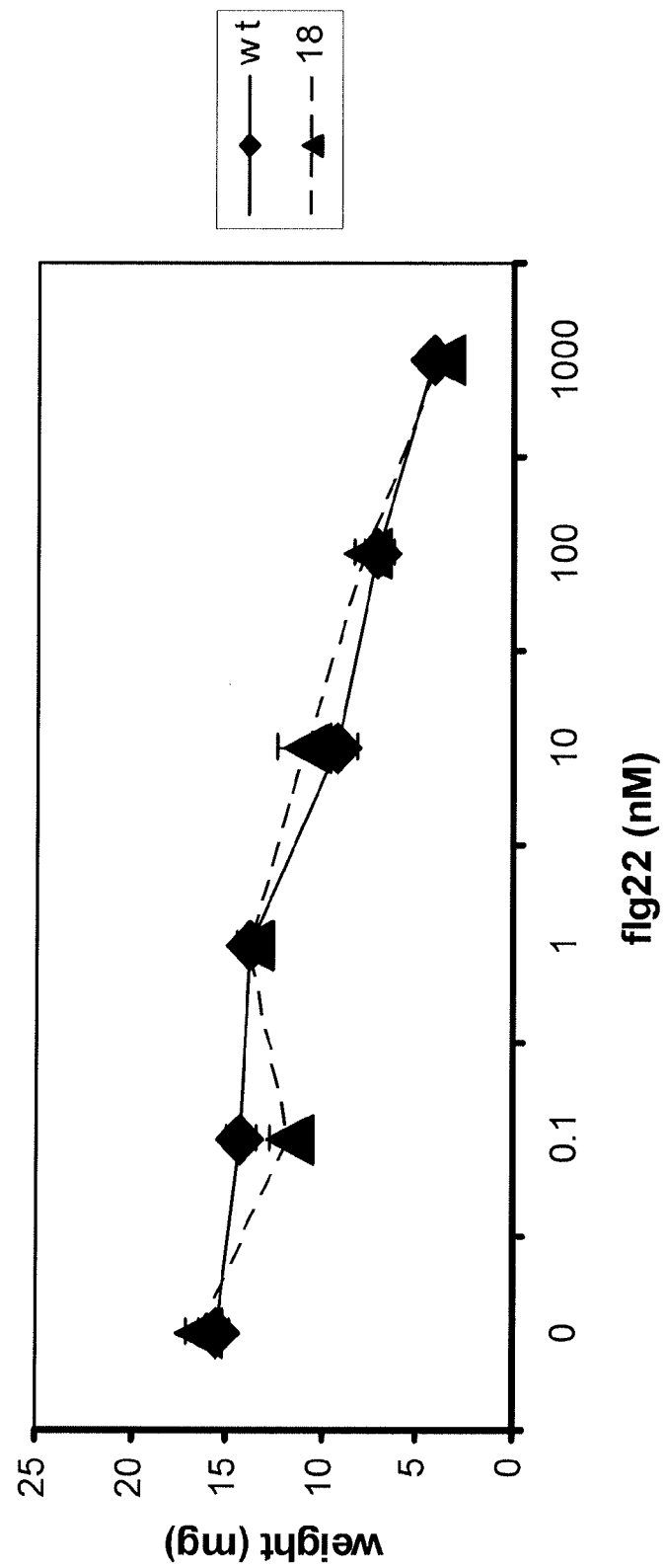
Figure 3C:
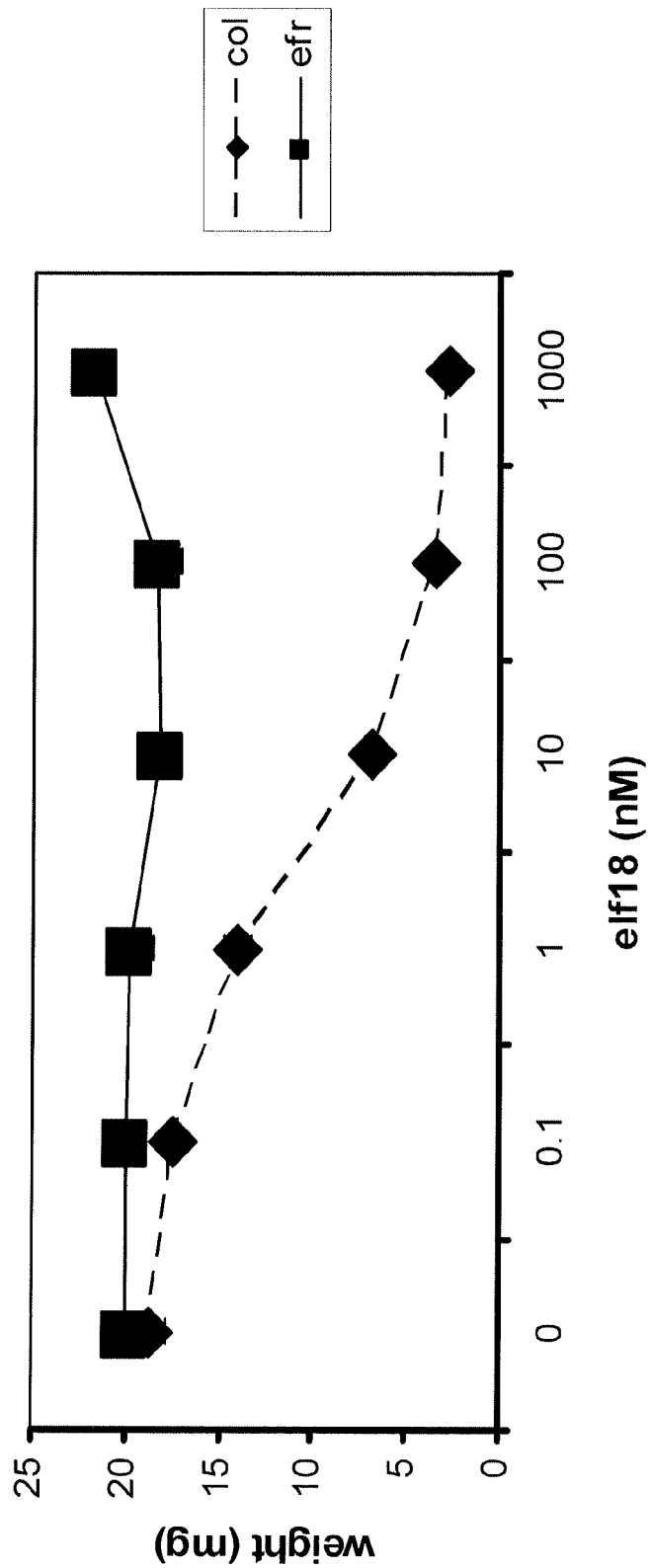
Figure 3D:
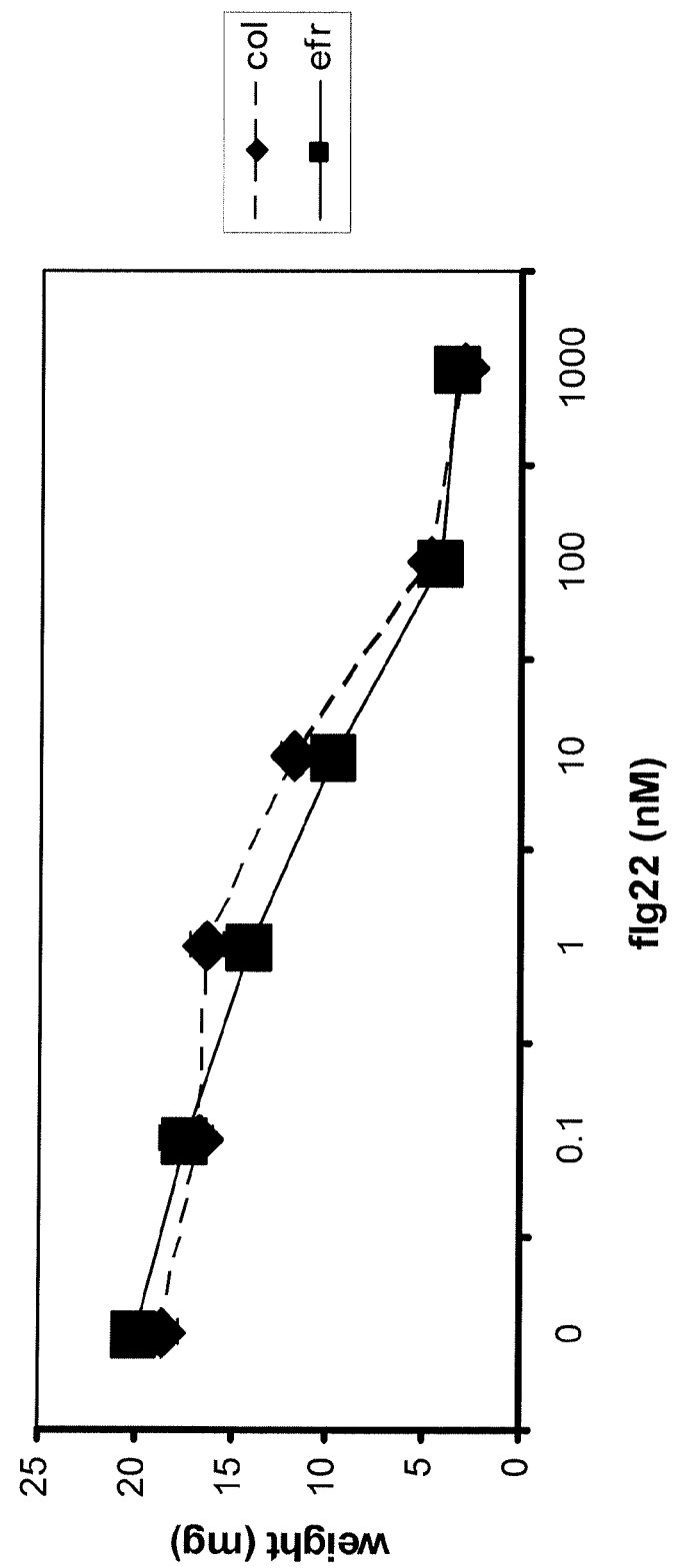

Pathogen attacks occur throughout a plant's life. Therefore, even a freshly germinated seedling needs the ability to respond to attempted colonisation. This response is commonly observed as an inhibition of seedling growth. This response has been well characterized in *Arabidopsis* (Zipfel et al. (2006) *Cell* 125:749-760). Wild-type Col plants express EFR which detects the elf18 epitope, causing decreasing growth as elf18 concentration increases (FIG. 3B). By contrast, efr plants, which do not express functional EFR, grow normally because they are insensitive to elf18 (FIG. 3B). The response to flg22 is unaffected in efr (FIG. 3D). This same assay can be used to characterize Nb expressing transgenic AtEFR. Wild-type Nb plants do not express EFR so are able to grow in the presence of up to 1000 nM elf18 (FIG. 3A). This shows that growth inhibition is not caused by a possible toxic effect of the peptide but really is an active response. Crucially, EFR plants are responsive to the elf18 epitope (FIG. 3A). The sensitivity of seedling growth inhibition is similar to that see in wild-type Col (FIG. 3B). This indicates the heterologously transferred AtEFR is able to interact with equivalent downstream components present in Nb to produce the corresponding response. Once again, the response to flg22 is unaffected (FIG. 3C) and has a similar sensitivity to that of wild-type Col (FIG. 3D).

Enhanced Resistance of Transgenic Nb to Bacterial Disease

Clearly the data so far indicates that the expression of AtEFR in Nb confers the ability to perceive the epitope elf18 and trigger several responses associated with general defense. It is now essential to test the biological relevance of this information. The crucial test is to ensure that this data correlates with the capability of the transgenic plant to perceive virulent bacteria and retard their growth, reducing the appearance of symptoms. Preliminary results implied an increased resistance to the virulent bacterium *Pseudomonas syringae* pv. *tabaci* (data not shown). Confirmation of this result was achieved through disease scoring and growth curves following bacterial infections.

A total of five bacterial strains from four different pathovars were used in order to get an idea of the breadth of resistance conferred by expression of AtEFR. *Pseudomonas syringae* is a Gram-negative species in the class Gamma Proteobacteria. Three different pathovars were used in infection assays. (i) *Pseudomonas syringae* pv. *syringae* (Pss) mainly targets species in the genera *Syringa* and *Phaseolus*, but the strain B728a is also highly virulent on Nb. (ii) *Pseudomonas syringae* pv. *tabaci* 6665 and 11528 (Pstab) are both strains responsible for wildfire disease of tobacco. The bacteria produce a toxin, tabtoxin, which causes conspicuous chlorotic halos to develop around infection sites. (iii) *Pseudomonas syringae* pv. *Tomato* DC3000 (Pst) is the cause of bacterial speck on tomato but is also able to infect Nb. In addition, *Xanthomonas campestris* pv. *campestris* (Xcc) is also a member of Gamma Proteobacteria. The strain 8004 is the causal agent of black rot in the Brassicaceae family but is also mildly virulent on Nb.

These bacteria were individually inoculated onto wild-type and EFR plants and sampled daily to form a timecourse of infection. Initially the Pstab 6665 strain was used, however although these bacteria successfully colonised the wild-type plant, no symptoms were displayed (data not shown). In subsequent experiments Pstab 11528 was used and is able to both colonise and cause symptoms on wild-type plants. The Xcc 8004 never reached a high colony count in wild-type Nb and never produced any symptoms, though this may be due to using an inadequate method of inoculation for this genus rather than a lack of virulence.

Figure 4:
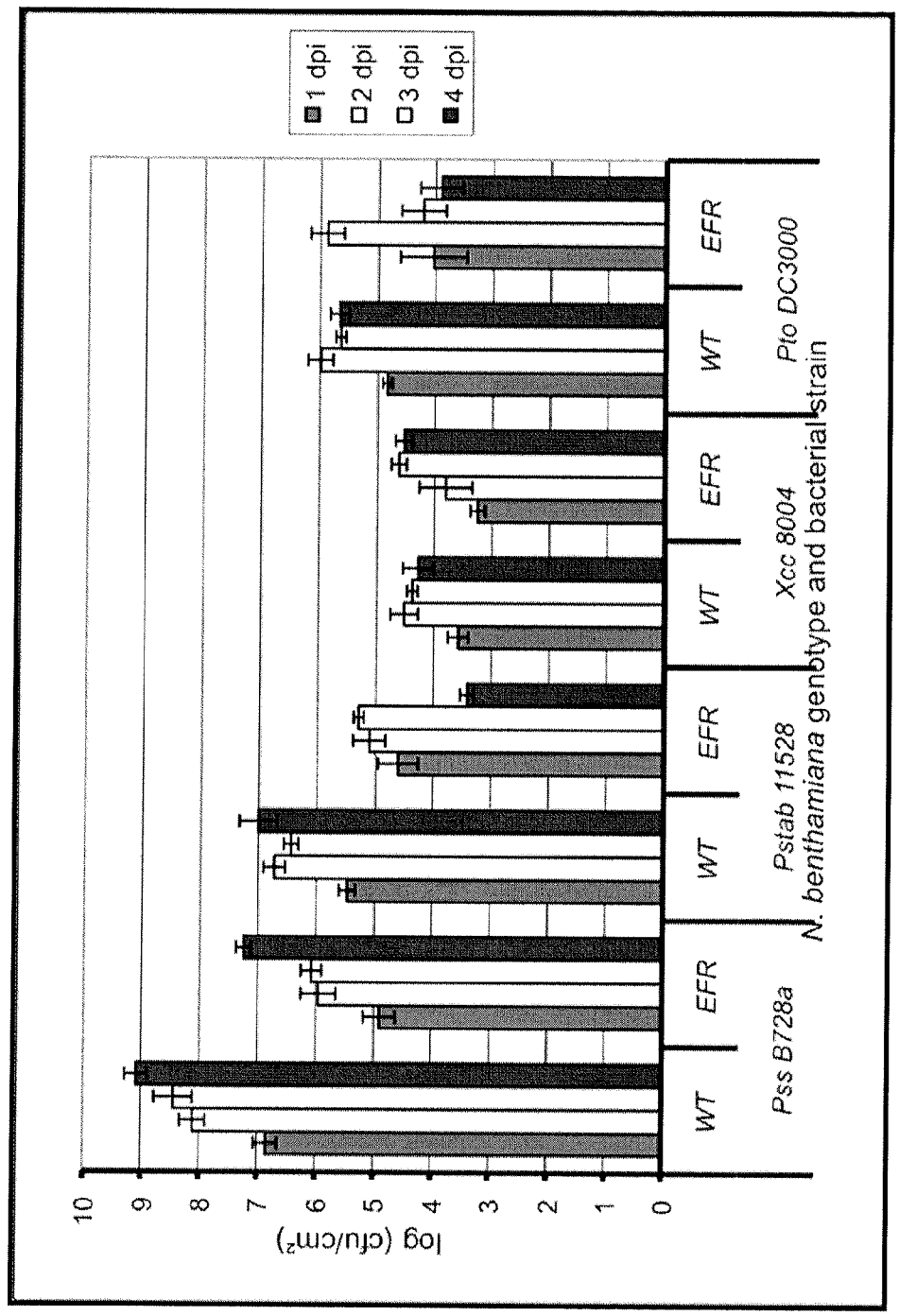
FIG. 4. Bacterial susceptibility in wild-type and EFR transgenic *N. benthamiana*. Bacterial growth curves of 4 different pathovars inoculated by spraying over 4 days. Data plotted represents an average±SE (n=4).

However a good comparison can be made between the three *Pseudomonas* species: Pss B728a, Pstab 11528 and Pst DC3000. Four days after spray inoculation with Pss B728a, there are 100-times more bacteria on wild-type Nb compared to EFR plants (FIG. 4). Pss B728a growth after inoculation by infiltration is also higher on wild-type plants (FIG. 4). Pstab 11528 inoculation displays an even more striking result. This highly virulent strain is 5000 times more abundant after spraying onto wild-type Nb rather than EFR plants (FIG. 4). Likewise Pst DC3000 grows nearly 100 times more successfully on wild-type Nb (FIG. 4). Both methods of inoculation show that over a period of several days, the expression of AtEFR restricts the ability of the pathogen to colonise the plant. Spray inoculation shows the clearest distinction with the EFR plants having a colony count up to 3.5 orders of magnitude lower than wild-type plants. This data indicates the breadth of resistance conferred by AtEFR expression. Transgenic Nb is less susceptible to a range of *Pseudomonas* species, so may be a way of introducing broad-spectrum disease control.

Figure 5:
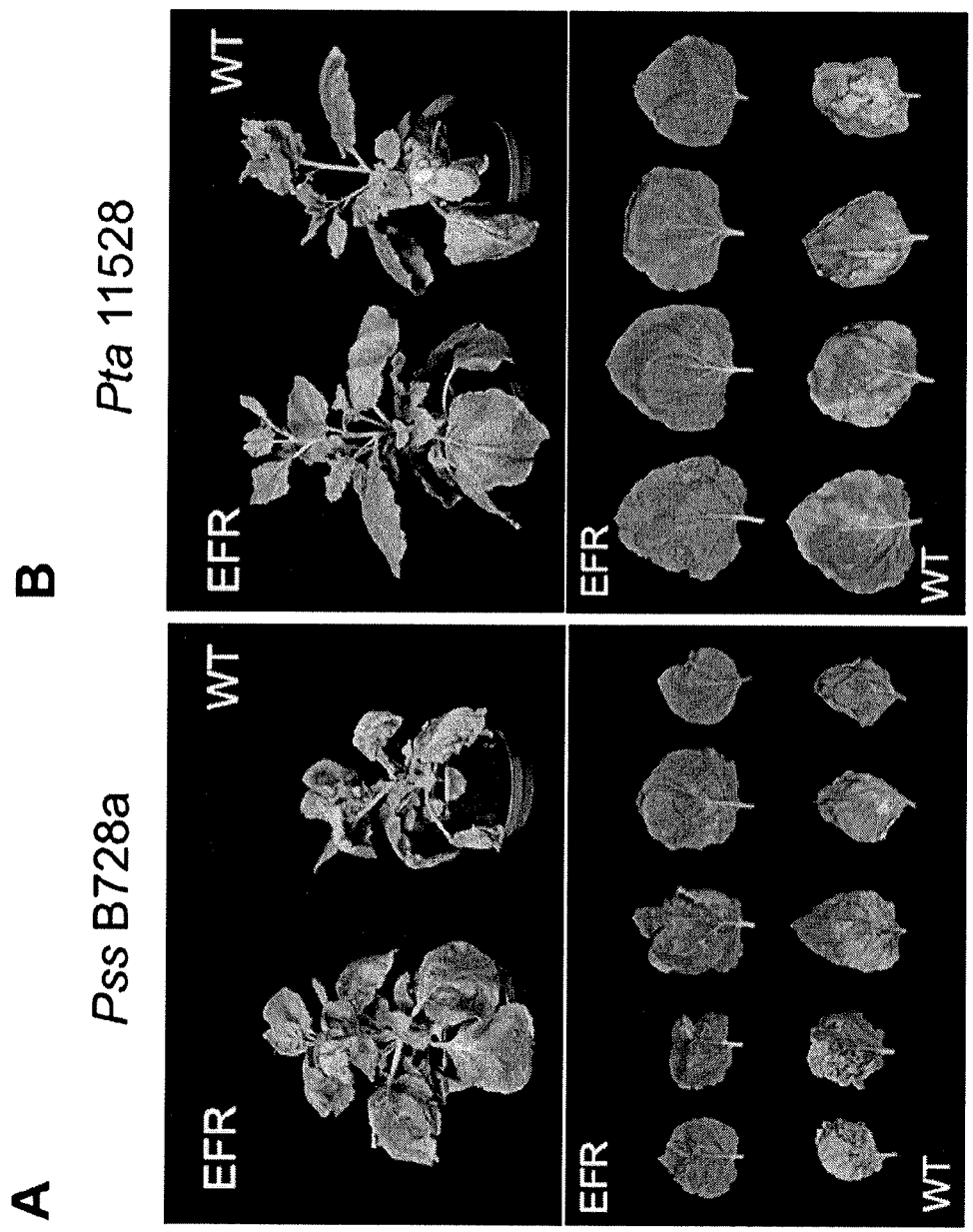
FIG. 5. Disease symptoms in wild-type and EFR transgenic *N. benthamiana* plants. Leaves and whole plant photos taken 10 days after spray-inoculation with Pss B728a (A and E), Pstab 11528 (B).

This difference in bacterial number is reflected in observable symptoms on leaves (FIG. 5A-B). The wild-type leaves are clearly very diseased with a number of necrotic spots and chlorotic patches, whereas the EFR leaves show fewer symptoms. The most virulent bacterium is Pss B728a which demonstrates differential colonisation ability at the whole plant level (FIG. 5A). After inoculation, the wild-type plant quickly displayed small necrotic spots which developed to cause extensive wilting and necrosis as the disease advanced, producing a severe disease phenotype. In comparison, the EFR plant is a normal height, with plenty of new growth and appears relatively healthy. Thus the expression of AtEFR clearly enables a general defense response, leading to reduced susceptibility to a range of bacteria.

Susceptibility to *Agrobacterium tumefaciens*

Figure 6:
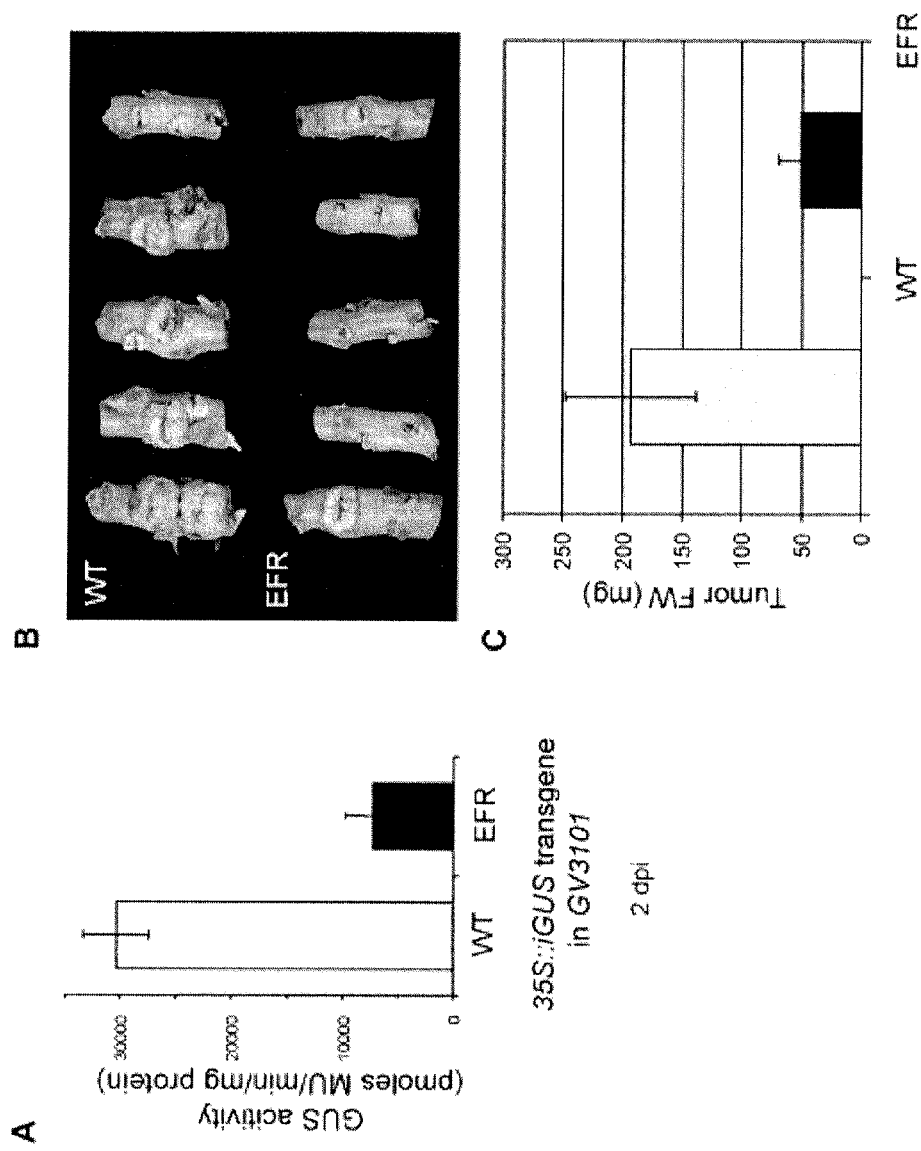
FIG. 6. Susceptibility of wild-type and EFR transgenic *N. benthamiana* to transgenic (GV3101/pBIN19-35S::GUS-HA) and wild-type tumorigenic (A281) *Agrobacterium tumefaciens*. (A) Quantitative analysis of transient GUS expression 2 days after agro-infiltration. (B) Pictures of crown galls 3 weeks following stem stabbing with A281. (C) Average fresh weight of excised galls (n=15)±SE (C).

Previous work on *Arabidopsis thaliana* demonstrated that efr mutant plants were more amenable to *Agrobacterium*-mediated transient expression than wild-type plants (Zipfel et al. (2006) *Cell* 125:749-760). Thus *Agrobacterium* PAMPs, such as EF-Tu, triggers the activation of plant defenses and restricts plant transformation. This is now further substantiated by comparing the efficiency of *Agrobacterium*-mediated transient expression on wild-type and EFR Nb. FIG. 6A depicts marginally more intensive GUS staining in wild-type discs compared to EFR. Furthermore, a test was conducted to determine whether EFR plants are less susceptible to the wild-type tumorigenic *Agrobacterium tumefaciens* strain A281. FIG. 6B shows large crown galls formed on wildtype Nb stems, while gall formation was strongly reduced on EFR Nb stems. When weighed, the galls are nearly four times lighter on Nb stems expressing EFR compared to wild-type (FIG. 6C). Thus, while mutating EFR might be a key to improve the efficiency of *Agrobacterium*-mediated transformation in Brassicaceae, EFR transgenesis could be used to render plants more resistant to grown-gall disease.

Non-Constitutive Expression of Defense Genes in Transgenic Nb

An essential control was to ensure that transgenic AtEFR expression does not lead to constitutive activation of defense genes. The expression of the marker transcript PR-1 was measured in plants first grown in sterile conditions, then transferred to soil. Virtually no expression of the basic PR-1 gene was detected in EFR plants, even when grown in non-sterile conditions for over 4 weeks (data not shown). However, weak expression of the acidic PR-1 gene was observed in EFR plants and in 5 and 6 week-old wild-type plants (data not shown). Thus potential biotic stress caused by growth in non-sterile conditions does not result in drastic defense activation in EFR plants, compared to wild-type.

Discussion

These results provide a molecular and physiological characterization of *Nicotiana benthamiana* expressing AtEFR. The evidence indicates that stable expression of the transgenic receptor confers the ability to perceive the epitope elf18, inducing a number of defense responses associated with PAMP-triggered immunity (PTI). Furthermore in pathogenicity tests, transgenic expression of AtEFR in Nb inhibits bacterial invasion and colonisation, resulting in a lower bacterial colony count and reduction in observable symptoms. This result was detected for a range of bacterial pathovars and transgenic EFR plants were also more resistant to crown-gall disease, indicating the expression of AtEFR confers broad-spectrum resistance. Clearly this approach can lead to plants with improved resistance to bacterial disease.

The perception of PAMPs by plants is now recognised as an important part of plant defense. But although many PAMPs have been identified, few PRRs are known, leaving the opportunity for many more to be discovered. *Arabidopsis* encodes 610 receptor-like kinases (RLKs), over 50 receptor-like proteins (RLPs) and around 150 nucleotide-binding site plus leucine-rich repeats (NBS-LRRs). As FLS2 and EFR are both RLKs, it is likely that other RLKs will perceive PAMPs. Although 20% of *Arabidopsis thaliana* RLKs are putatively enzymatically inactive due to a mutation in a conserved residue, they may still function in signalling through phosphorylation-independent mechanisms (Castells and Casacuberta (2007) *Journal of experimental Botany* 58:3503-3511). Despite the lack of known plant PRRs from the NBS-LRR family, several members are plant R genes, while in mammals several NBS-LRRs have been identified as intracellular PRRs. In time, the discovery of further PRRs in model plants, may enable their heterologous expression to produce crops with greater disease resistance.

Yet any increase in disease resistance is often only transient. Loss of resistance is accelerated through growth in monocultures which exert a strong selection pressure on the pathogen. Consequently the pathogen evolves to avoid recognition by either accumulating mutations in the relevant gene or losing it completely. This lack of durability is particularly common when heterologously expressing R genes detecting microbial elicitors which can be lost without affecting microbial virulence. This led to a search for essential pathogenicity genes, resulting in the identification of the AvrBs2 gene which is crucial for the fitness of *Xanthomonas campestris* pv. *vesicatoria*. Subsequently the corresponding R gene, Bs2, was cloned from pepper and successfully transferred to tomato where it conferred durable resistance (Tai et al. (1999) *Proc. Natl. Acad. Sci. USA* 96:14153-14158). In contrast to R genes, PAMPs are essential microbial molecules which are not easily mutated without conferring a selective disadvantage. Thus the transfer of PRRs able to recognise PAMPs holds great promise for creating sustainable resistance.

However, several potential problems remain. Effective innate immunity requires the PRR to be active in all tissues which could be attacked, however there is little information on PRR expression patterns. The solution to this is either to find natural promoters which could be adapted for use or synthesise new ones (Gurr and Rushton (2005) *Trends Biotechnol.* 14:283-290). Synthetic promoters could be designed to be induced only in the presence of a pathogen, which would limit expression of defense reactions to the infection site, ensuring efficient expression. Another potential problem is that increased levels of resistance could cause a decrease in yield. This is common when employing strategies such as 'pyramiding' of R genes, because the constitutive expression of defense pathways occurs even in the absence of a pathogen. This consumes resources which are needed for growth and so could actually lead to a reduction in plant fitness (Jones (2001) *Curr. Opin. Plant Biol.* 4: 281-287). As well as the use of pathogen inducible promoters, other strategies to avoid this include engineering plants so that the balance of defense is shifted to combating one particular pathogen more successfully whilst avoiding the consequences of increased susceptibility to other pathogens by changing other parameters such as the growth conditions (Stuiver and Custers (2001) *Nature* 411:865-868). In all cases, a small decrease in yield is likely but this should be compensated by the benefits of increased yield stability (Walters and Boyle (2005) *Physiol. and Mol. Plant P.* 66:40-44).

Example 2

Characterization of Transgenic Tomato Stably Expressing AtEFR

Characterization of Tomato and Potato Primary Transformants

In parallel to characterizing transgenic Nb, other members of the Solanaceae family, *Solanum lycopersicum* (tomato, var. Moneymaker) and *Solanum tuberosum* (potato, var. Desiree), were also used for a preliminary investigation. Fifteen primary transformants expressing AtEFRp::EFR and 21 expressing 35S::AtEFR for tomato, and 7 primary transformants expressing AtEFRp::EFR and 11 expressing 35S::AtEFR for potato were tested to identify lines that gained EF-Tu responsiveness for further physiological and molecular characterization.

Oxidative Burst: Luminol-Based Assay

To measure the production of reactive oxygen species (ROS) in leaf tissue, size #1 leaf discs (Nb; n=12, tomato and potato; n=8) were floated overnight in water. Each disc was then transferred to a well containing an assay mix of luminol (200 μM) and peroxidase (20 μg/ml) in 100 μl water. Each well was then treated with either: assay mix, 100 nm elf18, or 100 nm flg22. Luminescence in a 96-well plate was subsequently measured using a Flash Varioskan luminometer.

The detection of an oxidative burst is a relatively simple and reliable assay for defense activation. Cumulative luminescence was recorded for each plant over a time course of 40 minutes. Ten primary transformant tomato plants (numbers 1, 3, 10, 13, 14, 16, 20, 22, 33 and 36) were identified as positive lines because they displayed a considerable burst of ROS after elicitation with elf18 (data not shown). Several other transformants were unable to express functional AtEFR as they give very little response to elf18, yet are able to respond to flg22 elicitation (data not shown). Other transformants, perhaps due to old age, were unable to respond to elf18 or flg22 treatment (data not shown). The 10 positive lines appear to have acquired EF-Tu responsiveness in this assay. Therefore seeds were harvested to grow homozygous lines for use in further assays to confirm of these initial results.

Oxidative burst assays were also conducted with transgenic EFR potatoes (Desiree). Similar to the results with the tomato transformants, positive potato lines were identified that displayed a considerable burst of ROS after elicitation with elf18 (data not shown).

Infection Assays

Overnight bacterial liquid cultures were resuspended in water at an $OD_{600}$=0.2. After addition of Silwett-L77 0.04%, the bacterial solution was spray onto plants. Bacterial populations were measured at the indicated time-points by grinding leaf discs in water and plating serial dilutions onto plates to allow colony counting.

Example 3

Transformation of Banana with AtEFR

Embryogenic suspension cultures of banana are prepared as described (Côte et al. (1996) *Physiol. Plant.* 97:285-290). Embryogenic suspension cells are co-cultivated with *Agrobacterium* cells containing a T-DNA vector containing a chimeric AtEFR gene under the control of the maize polyubiquitin-1 promoter Becker et al. (2000) *Plant Cell Rep.* 19:229-234), and a selectable marker gene consisting of the NPTII coding sequence under the control of the 35S promoter. Transformed calli are selected on medium containing kanamycin. Transformed calli (i.e., kanamycin-resistant calli) are then regenerated into transformed banana plants using standard methods. See, U.S. Pat. No. 5,792,935 U.S. Pat. No. 6,133,035; May et al. (1995) *Biotechnology* 13:486-492; Dhed'a, et al. (1991) *Fruits* 46:125-135); Sagi, et al. (1995) *Biotechnology* 13:481-485; Marroquin et al. (1993) *In Vivo Cell. Div. Biol.* 29P:43-46; Ma (1991) "Somatic Embryogenesis and Plant Regeneration from Cell Suspension Culture of Banana", in *Proceedings of Symposium on Tissue Culture of Horicultural Crops*, Mar. 8-9, 1988, Department of Horticulture, National Taiwan University, Taipei, Taiwan, pp. 181-188; all of which are hereby incorporated herein in their entirety by reference.

Example 4

Elf18 Peptides from Diverse Phytopathogenic Bacteria are Active as PAMPs

Using available genomic information, synthetic peptides were obtained corresponding to elf18 peptides derived from EF-Tu sequences of relevant pythopathogenic bacteria. Based on sequence identity, these peptides group into 8 groups (FIG. 7). The elf18 region from *Candidatus Liberibacter asiaticus* str. Psy62, the causal agent of Citrus Greening, was identified recently but not yet tested for its eliciting activity. All peptides of the other peptide in FIG. 7 have been tested for their abilities to induce an oxidative burst in wild-type leaves of *Arabidopsis thaliana* Col-0. The elf18 peptides derived from *Xanthomonas campestris* pv *campestris* 8004 and B100 and *Pseudomonas syringae* pv. *syringae* DC3000 show a very low eliciting activity, while all the other peptides show activities equal of superior to the elf18 peptide derived from *Escherichia coli* used here as a positive control (FIG. 8). The differential activities of the peptides will be further tested in the future over a range of concentrations. This experiment clearly shows that recognition of EF-Tu will occur after exposure with many different phytopathogenic bacteria. Additional tests will be conducted with crude extracts from bacteria without known EF-Tu sequence to test for EF-Tu activity.

Example 5

Transgenic Tomatoes and Potatoes Stably Expressing AtEFR

The transgenic 35S::EFR tomatoes (*Solanum lycopersicum* cv. Moneymaker) described above in Example 2 were taken to T2 homozygous stage, and lines were confirmed that gained elf18 responsiveness (data not shown). Seeds are now available for these lines. Similarly the gain of elf18 responsiveness has been confirmed in several independent transgenic EFR potato lines (*Solanum tuberosum* cv. Desiree) (data not shown). Tubers are now available for these lines.

Two independent 35S::EFR tomato lines showed a strong disease resistance to the hyper-virulent bacterium *Ralstonia solanacearum* GMI1000 (FIG. 9), the causal agent of bacterial wilt in many Solanaceae species. These results demonstrate that the methods of the present invention approach can be used in economically relevant Solanaceae species and are also efficient against vascular pathogens that infect the plant via the roots.

Example 6

Resistance of Transgenic Tomato Expressing EFR to *Xanthomonas perforans*

T3 *Solanum lycopersicum* cv. Moneymaker lines transgenic for 35S::EFR were grown until true leaflets formed. *Xanthomonas perforans* T4 strain 4B (the causal agent of bacterial spot disease, also referred to as *Xanthomonas campestris* pv. *vesicatoria*) was grown overnight, and suspended in 1 mM $MgCl_2$, 0.008% Silwet L77 to an $OD_{600}$=0.01 (~$10^7$ cfu/mL). The first fully expanded true leaflet on each of 3 plants was repeatedly dipped into 500 mL of the bacterial suspension for 30 seconds. The leaves were air dried and a 1 cm² leaf disk was collected from each of the three plants. Each disk was ground in 1 mL of 1 mM $MgCl_2$, and 50 uL plated on rich agar medium containing 50 ug/mL each rifampicin (to select for the *X. perforans*) and cycloheximide (to inhibit fungal growth). This initial sampling was designated T=0. Each inoculated leaflet, still attached to the plants, was covered with a plastic bag for 3 days provide high humidity favoring bacterial growth. At 14 days after inoculation, leaf samples were collected, processed, and plated as described above, with 3 leaflet sampled for each genotype. Serial dilutions (between $10^{-2}$ and $10^{-7}$) were used to obtain useable colony counts. The entire experiment was carried out twice.

Figure 10:
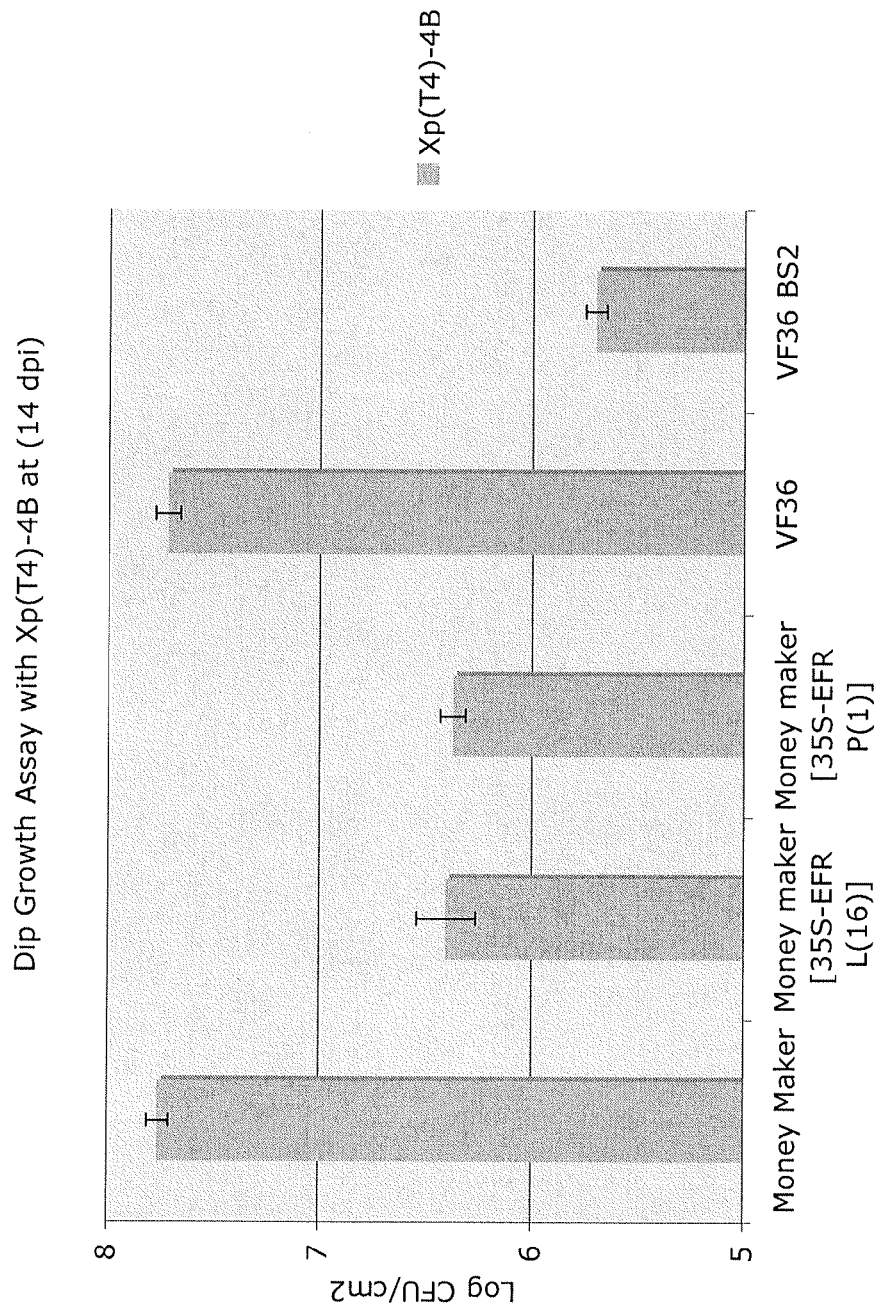
FIG. 10. Results of dip growth assay of two T3 *Solanum lycopersicum* cv. Moneymaker lines [L(16) and P(1)] transgenic for 35S::EFR with *Xanthomonas perforans* T4 strain 4B [Xp(T4)-4B] at 14 days post inoculation (dpi), replication 1. As a positive control, *S. lycopersicum* cv. VF36 expressing the major dominant R gene Bs2 from pepper was simultaneously infected. Negative controls are non-transgenic Moneymaker and VF36.
Figure 11:
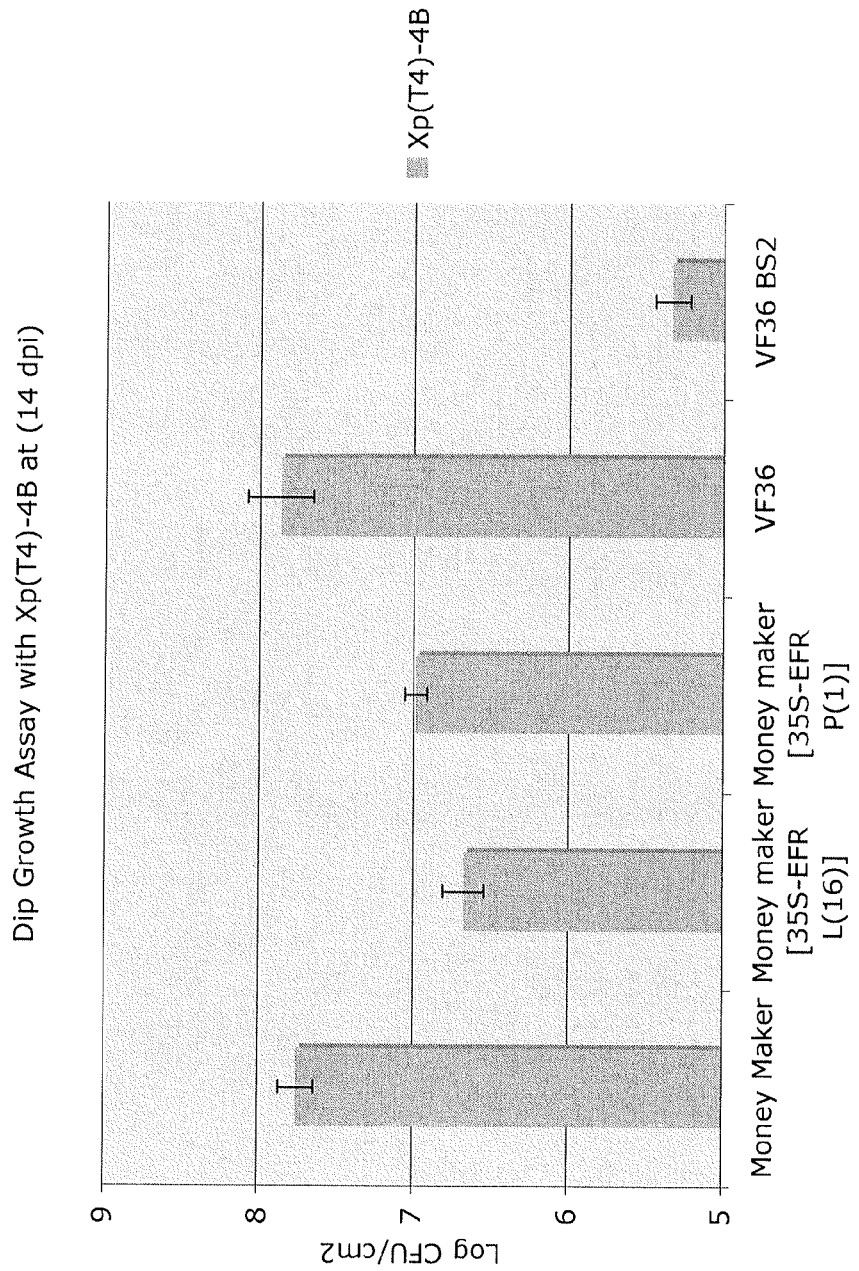
FIG. 11. Results of dip growth assay of two T3 *Solanum lycopersicum* cv. Moneymaker lines [L(16) and P(1)] transgenic for 35S::EFR with *Xanthomonas perforans* T4 strain 4B [Xp(T4)-4B] at 14 days post inoculation (dpi), replication 2. As a positive control, *S. lycopersicum* cv. VF36 expressing the major dominant R gene Bs2 from pepper was simultaneously infected. Negative controls are non-transgenic Moneymaker and VF36.

The results showed that control, untransformed Moneymaker supported growth of the bacterial to between $10^7$ and $10^8$ cfu/mL. The two independent lines expressing EFR [L(16) and P(1)] supported at least 10-fold less growth (FIGS. 10 and 11), clearly demonstrating the suppressive effect of EFR expression in tomato on growth of the pathogen *X. perforans*. As a positive control, *S. lycopersicum* cv. VF36 expressing the major dominant R gene Bs2 from pepper was simultaneously infected, and showed approximately 100-fold less growth than non-transgenic VF36 or Moneymaker.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. A method for enhancing the resistance of a Solanaceous plant to bacterial pathogens, said method comprising the steps of:
   (a) transforming a Solanaceous plant cell with a polynucleotide construct comprising a promoter and a nucleotide sequence that encodes an EF-Tu receptor (EFR), wherein said promoter is operably linked to said nucleotide sequence and said promoter is capable of driving expression of said nucleotide sequence in a plant cell, and wherein said nucleotide sequence is selected from the group consisting of (i) the nucleotide sequence set forth in SEQ ID NO: 1 or 3, (ii) a nucleotide sequence encoding the amino acid sequence set forth in SEQ ID NO: 2, and (iii) a nucleotide sequence encoding an amino acid sequence having at least 95% identity to the full-length of the amino acid sequence set forth in SEQ ID NO: 2, wherein said nucleotide sequence encodes a protein comprising EFR activity; and (b) regenerating a transformed plant from said transformed plant cell, wherein the polynucleotide construct is stably integrated into the genome the transformed plant;

wherein said transformed plant has enhanced resistance to at least two bacterial pathogens when compared to a wild-type plant.

2. The method of claim 1, wherein said nucleotide sequence encodes an *Arabidopsis thaliana* EF-Tu receptor (AtEFR).

3. The method of claim 1, wherein said nucleotide sequence is selected from the group consisting of the nucleotide sequences of (i) and (ii).

4. The method of claim 1, wherein said promoter is the AtEFR promoter.

5. The method of claim 4, wherein said promoter comprises SEQ ID NO: 5.

6. The method of claim 1, wherein the promoter is selected from the group consisting of constitutive promoters, pathogen-inducible promoters, tissue-preferred promoters, and chemical-regulated promoters.

7. The method of claim 1, wherein said transformed plant further comprises at least one R gene.

8. The method of claim 7, wherein said R gene comprises recombinant DNA.

9. The method of claim 1, wherein said transformed plant further comprises a nucleotide sequence encoding the Bs2 protein, a nucleotide sequence encoding the Bs3 protein, or a nucleotide sequence encoding the Bs2 protein and a nucleotide sequence encoding the Bs3 protein.

10. The method of claim 9, wherein said plant is selected from the group consisting tomato, potato, tobacco, and pepper.

* * * * *